(12) United States Patent
Schaak

(10) Patent No.: US 11,920,126 B2
(45) Date of Patent: Mar. 5, 2024

(54) BIO-MANUFACTURING PROCESS

(71) Applicant: Ecovative Design LLC, Green Island, NY (US)

(72) Inventor: Damen Schaak, Clifton Park, NY (US)

(73) Assignee: Ecovative Design LLC, Green Island, NY (US)

( * ) Notice: Subject to any disclaimer, the term of this patent is extended or adjusted under 35 U.S.C. 154(b) by 227 days.

(21) Appl. No.: 16/363,052

(22) Filed: Mar. 25, 2019

(65) Prior Publication Data

US 2019/0322997 A1 Oct. 24, 2019
US 2021/0317433 A9 Oct. 14, 2021

Related U.S. Application Data

(60) Provisional application No. 62/649,175, filed on Mar. 28, 2018.

(51) Int. Cl.

| | |
|---|---|
| *C12N 11/02* | (2006.01) |
| *A01G 18/10* | (2018.01) |
| *A23K 10/18* | (2016.01) |
| *A23K 40/30* | (2016.01) |
| *C12N 1/00* | (2006.01) |
| *C12N 1/02* | (2006.01) |
| *C12N 1/14* | (2006.01) |
| *C12N 1/20* | (2006.01) |
| *C12N 9/80* | (2006.01) |
| *C12N 9/88* | (2006.01) |
| *C12N 11/14* | (2006.01) |
| *C12N 15/00* | (2006.01) |
| *C12N 15/52* | (2006.01) |
| *C12N 15/74* | (2006.01) |
| *C12N 15/76* | (2006.01) |
| *C12N 15/80* | (2006.01) |
| *C12R 1/07* | (2006.01) |
| *C12R 1/125* | (2006.01) |
| *C12R 1/465* | (2006.01) |

(52) U.S. Cl.
CPC ............. *C12N 11/02* (2013.01); *A01G 18/10* (2018.02); *A23K 10/18* (2016.05); *A23K 40/30* (2016.05); *C12N 1/00* (2013.01); *C12N 1/02* (2013.01); *C12N 1/14* (2013.01); *C12N 1/205* (2021.05); *C12N 9/80* (2013.01); *C12N 9/88* (2013.01); *C12N 11/14* (2013.01); *C12N 15/00* (2013.01); *C12N 15/52* (2013.01); *C12N 15/746* (2013.01); *C12N 15/76* (2013.01); *C12N 15/80* (2013.01); *C12R 2001/07* (2021.05); *C12R 2001/125* (2021.05); *C12R 2001/465* (2021.05); *C12Y 305/01041* (2013.01); *C12Y 402/01001* (2013.01)

(58) Field of Classification Search
CPC .......... C12N 1/205; C12N 9/88; C12N 15/00; C12N 15/76; C12N 15/80; C12R 2001/07; C12R 2001/465; C12Y 305/01041; C12Y 402/01001

See application file for complete search history.

(56) References Cited

U.S. PATENT DOCUMENTS

| | | |
|---|---|---|
| 1,979,176 A | 10/1934 | Schicht |
| 2,509,984 A | 5/1950 | Morrow |
| 2,657,647 A | 11/1953 | Rapisarda |
| 2,723,493 A | 11/1955 | Stoller |
| 2,815,621 A | 12/1957 | Carter |
| 2,964,070 A | 12/1960 | Linhardt |
| 3,268,606 A | 8/1966 | Jaeger |
| 3,316,592 A | 5/1967 | Forrest |
| 3,317,375 A | 5/1967 | Molinet et al. |
| 3,421,554 A | 1/1969 | Carter |
| 3,477,558 A | 11/1969 | Fleischauer |
| 3,499,261 A | 3/1970 | Hullhorst et al. |
| 3,708,952 A | 1/1973 | Schulze et al. |
| 3,717,953 A | 2/1973 | Kuhn et al. |
| 3,782,033 A | 1/1974 | Hickerson |
| 3,810,327 A | 5/1974 | Giansante |
| 3,828,470 A | 8/1974 | Stoller |
| 3,885,048 A | 5/1975 | Liggett |
| 3,911,141 A | 10/1975 | Farr et al. |
| 3,961,938 A | 6/1976 | Iizuka et al. |
| 4,027,427 A | 6/1977 | Stoller et al. |
| 4,036,122 A | 7/1977 | Langen |

(Continued)

FOREIGN PATENT DOCUMENTS

| | | |
|---|---|---|
| CN | 1059662 A | 3/1992 |
| CN | 1273249 A | 11/2000 |

(Continued)

OTHER PUBLICATIONS

Huang et al., Applied and Environmental Microbiology, 2015, vol. 81, No. 19, p. 6718-6724.*

(Continued)

*Primary Examiner* — Kade Ariani
(74) *Attorney, Agent, or Firm* — Knobbe, Martens, Olson & Bear, LLP

(57) ABSTRACT

The process of making a biocomposite material utilize a bacterial species and a fungal species in an agricultural feedstock composed of a substrate of non-nutrient discrete particles and a nutrient material wherein the bacterial species imparts mechanical properties to the biocomposite material and the fungal species binds the biocomposite material. Both bacterium and fungus can be genetically engineered to produce desired properties within the microbial communities.

24 Claims, No Drawings

(56) References Cited

U.S. PATENT DOCUMENTS

| | | |
|---|---|---|
| 4,038,807 A | 8/1977 | Beardsley et al. |
| 4,063,383 A | 12/1977 | Green |
| 4,073,956 A | 2/1978 | Yates |
| 4,127,965 A | 12/1978 | Mee |
| 4,136,767 A | 1/1979 | Sarovich |
| 4,226,330 A | 10/1980 | Butler |
| 4,233,266 A | 11/1980 | Kummer |
| 4,263,744 A | 4/1981 | Stoller |
| 4,265,915 A | 5/1981 | MacLennan et al. |
| 4,294,929 A | 10/1981 | Solomons et al. |
| 4,337,594 A | 7/1982 | Hanacek et al. |
| 4,370,159 A | 1/1983 | Holtz |
| 4,568,520 A | 2/1986 | Ackermann et al. |
| 4,620,826 A | 11/1986 | Rubio et al. |
| 4,716,712 A | 1/1988 | Gill |
| 4,722,159 A | 2/1988 | Watanabe et al. |
| 4,878,312 A | 11/1989 | Shimizu |
| 4,922,650 A | 5/1990 | Akao et al. |
| 4,960,413 A | 10/1990 | Sagar et al. |
| 5,021,350 A | 6/1991 | Jung et al. |
| 5,030,425 A | 7/1991 | Bowers-Irons et al. |
| 5,074,959 A | 12/1991 | Yamanaka et al. |
| 5,085,998 A | 2/1992 | Lebron et al. |
| 5,088,860 A | 2/1992 | Stockdale et al. |
| 5,123,203 A | 6/1992 | Hiromoto |
| 5,230,430 A | 7/1993 | Kidder |
| 5,306,550 A | 4/1994 | Nishiyama et al. |
| 5,335,770 A | 8/1994 | Baker et al. |
| 5,370,714 A | 12/1994 | Ogawa |
| 5,433,061 A | 7/1995 | Hutchinson et al. |
| 5,440,860 A | 8/1995 | Meli et al. |
| 5,475,479 A | 12/1995 | Hatakeyama et al. |
| 5,498,384 A | 3/1996 | Volk et al. |
| 5,503,647 A | 4/1996 | Dahlberg et al. |
| 5,511,358 A | 4/1996 | Morita et al. |
| 5,532,217 A | 7/1996 | Silver et al. |
| 5,569,426 A | 10/1996 | Le Blanc |
| 5,589,390 A | 12/1996 | Higuchi et al. |
| 5,590,489 A | 1/1997 | Hattori et al. |
| 5,598,876 A | 2/1997 | Zanini et al. |
| 5,606,836 A | 3/1997 | Insalaco et al. |
| 5,647,180 A | 7/1997 | Billings et al. |
| 5,681,738 A | 10/1997 | Beelman et al. |
| 5,682,929 A | 11/1997 | Maginot et al. |
| 5,685,124 A | 11/1997 | Jandl |
| 5,711,353 A | 1/1998 | Ichikawa et al. |
| 5,802,763 A | 9/1998 | Milstein |
| 5,854,056 A | 12/1998 | Dschida |
| 5,888,803 A | 3/1999 | Starkey |
| 5,897,887 A | 4/1999 | Haeberli |
| 5,919,507 A | 6/1999 | Beelman et al. |
| 5,944,928 A | 8/1999 | Seidner |
| 5,948,674 A | 9/1999 | Mankiewicz |
| 5,979,109 A | 11/1999 | Sartor et al. |
| 6,041,544 A | 3/2000 | Kananen et al. |
| 6,041,835 A | 3/2000 | Price |
| 6,073,388 A | 6/2000 | Kananen et al. |
| 6,098,677 A | 8/2000 | Wegman et al. |
| 6,112,504 A | 9/2000 | McGregor et al. |
| 6,143,549 A | 11/2000 | Lamar et al. |
| 6,197,573 B1 | 3/2001 | Suryanarayan et al. |
| 6,226,962 B1 | 5/2001 | Eason et al. |
| 6,300,315 B1 | 10/2001 | Liu |
| 6,306,921 B1 | 10/2001 | Al Ghatta et al. |
| 6,329,185 B1 | 12/2001 | Kofod et al. |
| 6,349,988 B1 | 2/2002 | Foster et al. |
| 6,402,953 B1 | 6/2002 | Gorovoj et al. |
| 6,425,714 B1 | 7/2002 | Waddell |
| 6,444,437 B1 | 9/2002 | Sporleder et al. |
| 6,471,993 B1 | 10/2002 | Shastri et al. |
| 6,475,811 B1 | 11/2002 | Babcock |
| 6,482,942 B1 | 11/2002 | Vittori |
| 6,491,480 B2 | 12/2002 | Waddell |
| 6,500,476 B1 | 12/2002 | Martin et al. |
| 6,523,721 B1 | 2/2003 | Nomoto et al. |
| 6,603,054 B2 | 8/2003 | Chen et al. |
| 6,620,614 B1 | 9/2003 | Lüth et al. |
| 6,660,164 B1 | 12/2003 | Stover |
| 6,679,301 B2 | 1/2004 | Makino et al. |
| 6,726,911 B1 | 4/2004 | Jülich et al. |
| 6,737,065 B2 | 5/2004 | Song et al. |
| 7,043,874 B2 | 5/2006 | Wasser et al. |
| 7,073,306 B1 | 7/2006 | Hagaman |
| 7,122,176 B2 | 10/2006 | Stamets |
| 7,179,356 B2 | 2/2007 | Aksay et al. |
| 7,395,643 B2 | 7/2008 | Franchini et al. |
| 7,514,248 B2 | 4/2009 | Gower et al. |
| 7,573,031 B2 | 8/2009 | Behar et al. |
| 7,621,300 B2 | 11/2009 | Bonney et al. |
| 7,661,248 B2 | 2/2010 | Conti et al. |
| 7,754,653 B2 | 7/2010 | Hintz |
| 7,836,921 B2 | 11/2010 | Isomura et al. |
| 8,001,719 B2 | 8/2011 | Bayer et al. |
| 8,205,646 B2 | 6/2012 | Isomura et al. |
| 8,227,224 B2 | 7/2012 | Kalisz et al. |
| 8,227,233 B2 | 7/2012 | Kalisz et al. |
| 8,241,415 B2 | 8/2012 | Wantling et al. |
| 8,298,809 B2 | 10/2012 | Kalisz et al. |
| 8,298,810 B2 | 10/2012 | Rocco et al. |
| 8,313,939 B2 | 11/2012 | Kalisz et al. |
| 8,517,064 B2 | 8/2013 | Isomura et al. |
| 8,658,407 B2 | 2/2014 | Lyons et al. |
| 8,763,653 B2 | 7/2014 | Weigel et al. |
| 8,999,687 B2 | 4/2015 | Bayer et al. |
| 9,068,171 B2 | 6/2015 | Kelly et al. |
| 9,079,978 B2 | 7/2015 | Räsänen et al. |
| 9,085,763 B2 | 7/2015 | Winiski et al. |
| 9,253,889 B2 | 2/2016 | Bayer et al. |
| 9,332,779 B2 | 5/2016 | Marga |
| 9,394,512 B2 | 7/2016 | Bayer et al. |
| 9,469,838 B2 | 10/2016 | Schaak et al. |
| 9,485,917 B2 | 11/2016 | Bayer et al. |
| 9,555,395 B2 | 1/2017 | Araldi et al. |
| 9,714,180 B2 | 7/2017 | McIntyre et al. |
| 9,752,122 B2 | 9/2017 | Marga |
| 9,795,088 B2 | 10/2017 | Bayer et al. |
| 9,801,345 B2 | 10/2017 | Bayer et al. |
| 9,803,171 B2 | 10/2017 | Bayer et al. |
| 9,879,219 B2 | 1/2018 | McIntyre et al. |
| 9,914,906 B2 | 3/2018 | Winiski et al. |
| 10,125,347 B2 | 11/2018 | Winiski |
| 10,144,149 B2 | 12/2018 | Araldi et al. |
| 10,154,627 B2 | 12/2018 | McIntyre et al. |
| 10,172,301 B2 | 1/2019 | McNamara et al. |
| 10,266,695 B2 | 4/2019 | Lucht et al. |
| 10,407,675 B2 | 9/2019 | Bayer et al. |
| 10,525,662 B2 | 1/2020 | Bayer et al. |
| 10,533,155 B2 | 1/2020 | Kozubal et al. |
| 10,537,070 B2 | 1/2020 | Betts et al. |
| 10,575,579 B2 | 3/2020 | Egeland et al. |
| 10,577,579 B2 | 3/2020 | Kozubal et al. |
| 10,583,626 B2 | 3/2020 | Bayer et al. |
| 10,589,489 B2 | 3/2020 | Bayer et al. |
| 10,590,379 B2 | 3/2020 | Kozubal et al. |
| 10,687,482 B2 | 6/2020 | Ross et al. |
| 10,785,925 B2 | 9/2020 | McNamara et al. |
| 11,001,801 B2 | 5/2021 | Kozubal et al. |
| 11,015,168 B2 | 5/2021 | Kozubal et al. |
| 11,149,247 B2 | 10/2021 | Harney et al. |
| 11,261,420 B2 | 3/2022 | Kozubal et al. |
| 11,266,085 B2 | 3/2022 | Kaplan-Bie et al. |
| 11,272,726 B2 | 3/2022 | Macur et al. |
| 11,277,979 B2 | 3/2022 | Greetham et al. |
| 11,277,981 B2 | 3/2022 | Ross |
| 11,293,005 B2 | 4/2022 | Carlton et al. |
| 11,297,866 B2 | 4/2022 | Kozubal et al. |
| 11,343,979 B2 | 5/2022 | Mueller et al. |
| 11,359,074 B2 | 6/2022 | Kaplan-Bie et al. |
| 11,359,174 B2 | 6/2022 | Winiski et al. |
| 11,407,973 B2 | 8/2022 | Harney et al. |
| 11,420,366 B2 | 8/2022 | McIntyre et al. |
| 11,432,575 B2 | 9/2022 | Macur et al. |
| 11,459,541 B2 | 10/2022 | Harney et al. |
| 11,464,251 B2 | 10/2022 | Kozubal et al. |

(56) References Cited

U.S. PATENT DOCUMENTS

| | | |
|---|---|---|
| 11,466,245 B2 | 10/2022 | Harney et al. |
| 11,478,007 B2 | 10/2022 | Macur et al. |
| 11,505,779 B2 | 11/2022 | Kozubal et al. |
| 11,666,080 B2 | 6/2023 | Kozubal et al. |
| 2001/0012235 A1 | 8/2001 | Schuchardt |
| 2002/0110427 A1 | 8/2002 | Waddell |
| 2002/0131828 A1 | 9/2002 | Waddell |
| 2002/0131933 A1 | 9/2002 | Delmotte |
| 2003/0017565 A1 | 1/2003 | Echigo et al. |
| 2003/0056451 A1 | 3/2003 | Plsek et al. |
| 2003/0121201 A1 | 7/2003 | Dahlberg et al. |
| 2003/0157219 A1 | 8/2003 | Bijl et al. |
| 2003/0232895 A1 | 12/2003 | Omidian et al. |
| 2004/0000090 A1 | 1/2004 | Miller |
| 2004/0020553 A1 | 2/2004 | Amano |
| 2004/0166576 A1 | 8/2004 | Sadaie |
| 2004/0177585 A1 | 9/2004 | Vermette |
| 2004/0211721 A1 | 10/2004 | Stamets |
| 2005/0053778 A1 | 3/2005 | Hukkanen |
| 2005/0133536 A1 | 6/2005 | Kelsey et al. |
| 2005/0137272 A1 | 6/2005 | Gaserod et al. |
| 2006/0121006 A1 | 6/2006 | Chancellor et al. |
| 2006/0134265 A1 | 6/2006 | Beukes |
| 2006/0280753 A1 | 12/2006 | McNeary |
| 2007/0079944 A1 | 4/2007 | Amidon et al. |
| 2007/0196509 A1 | 8/2007 | Riman et al. |
| 2007/0225328 A1 | 9/2007 | Fritz et al. |
| 2007/0227063 A1 | 10/2007 | Dale et al. |
| 2007/0294939 A1 | 12/2007 | Spear et al. |
| 2008/0017272 A1 | 1/2008 | Isomura et al. |
| 2008/0046277 A1 | 2/2008 | Stamets |
| 2008/0047966 A1 | 2/2008 | Carson |
| 2008/0145577 A1 | 6/2008 | Bayer et al. |
| 2008/0234210 A1 | 9/2008 | Rijn et al. |
| 2008/0295399 A1 | 12/2008 | Kawai et al. |
| 2008/0296295 A1 | 12/2008 | Kords et al. |
| 2009/0107040 A1 | 4/2009 | Vandnhove |
| 2009/0111163 A1 | 4/2009 | Hoang et al. |
| 2009/0191289 A1 | 7/2009 | Lutz et al. |
| 2009/0241623 A1 | 10/2009 | Matano et al. |
| 2009/0246467 A1 | 10/2009 | Delantar |
| 2009/0272758 A1 | 11/2009 | Karwacki et al. |
| 2009/0307969 A1 | 12/2009 | Bayer et al. |
| 2009/0321975 A1 | 12/2009 | Schlummer |
| 2010/0101190 A1 | 4/2010 | Dillon |
| 2010/0158976 A1 | 6/2010 | O'Brien et al. |
| 2010/0159509 A1 | 6/2010 | Xu et al. |
| 2010/0199601 A1 | 8/2010 | Boldrini et al. |
| 2010/0227931 A1 | 9/2010 | Kuwano et al. |
| 2010/0243135 A1 | 9/2010 | Pepper et al. |
| 2010/0326564 A1 | 12/2010 | Isomura et al. |
| 2011/0094154 A1 | 4/2011 | Joaquin |
| 2011/0108158 A1 | 5/2011 | Huwiler et al. |
| 2011/0265688 A1 | 11/2011 | Kalisz et al. |
| 2011/0268980 A1 | 11/2011 | Kalisz et al. |
| 2011/0269209 A1 | 11/2011 | Rocco et al. |
| 2011/0269214 A1 | 11/2011 | Kalisz et al. |
| 2011/0306107 A1 | 12/2011 | Kalisz et al. |
| 2012/0000165 A1 | 1/2012 | Williams |
| 2012/0006446 A1 | 1/2012 | Isomura et al. |
| 2012/0060446 A1 | 3/2012 | Merz |
| 2012/0076895 A1 | 3/2012 | Kirejevas et al. |
| 2012/0115199 A1 | 5/2012 | Li et al. |
| 2012/0124839 A1 | 5/2012 | Kalisz et al. |
| 2012/0132314 A1 | 5/2012 | Weigel et al. |
| 2012/0135504 A1 | 5/2012 | Ross |
| 2012/0225471 A1 | 9/2012 | McIntyre et al. |
| 2012/0227899 A1 | 9/2012 | McIntyre et al. |
| 2012/0231140 A1 | 9/2012 | Hofmann et al. |
| 2012/0270031 A1 | 10/2012 | Guan et al. |
| 2012/0270302 A1 | 10/2012 | Bayer et al. |
| 2012/0315687 A1 | 12/2012 | Bayer et al. |
| 2013/0095560 A1 | 4/2013 | McIntyre et al. |
| 2013/0105036 A1 | 5/2013 | Smith et al. |
| 2013/0210327 A1 | 8/2013 | Corominas |
| 2013/0224840 A1 | 8/2013 | Bayer et al. |
| 2013/0274892 A1 | 10/2013 | Lelkes et al. |
| 2013/0309755 A1 | 11/2013 | McIntyre et al. |
| 2014/0038619 A1 | 2/2014 | Moulsley |
| 2014/0056653 A1 | 2/2014 | Scully et al. |
| 2014/0069004 A1 | 3/2014 | Bayer et al. |
| 2014/0093618 A1 | 4/2014 | Forgacs et al. |
| 2014/0120602 A1 | 5/2014 | Winiski et al. |
| 2014/0163142 A1 | 6/2014 | Zhang et al. |
| 2014/0173977 A1 | 6/2014 | Juscius |
| 2014/0371352 A1 | 12/2014 | Dantin et al. |
| 2015/0033620 A1 | 2/2015 | Greetham et al. |
| 2015/0038619 A1 | 2/2015 | McIntyre et al. |
| 2015/0101509 A1 | 4/2015 | McIntyre et al. |
| 2015/0197358 A1 | 7/2015 | Larsen |
| 2015/0342138 A1 | 12/2015 | Bayer et al. |
| 2015/0342224 A1 | 12/2015 | Medoff |
| 2016/0002589 A1 | 1/2016 | Winiski |
| 2016/0073589 A1 | 3/2016 | McNamara et al. |
| 2016/0264926 A1 | 9/2016 | Winiski et al. |
| 2016/0355779 A1 | 12/2016 | Ross |
| 2017/0000040 A1 | 1/2017 | Bayer et al. |
| 2017/0071214 A1 | 3/2017 | Rehage |
| 2017/0218327 A1 | 8/2017 | Amstislavski et al. |
| 2017/0253849 A1 | 9/2017 | Miller et al. |
| 2017/0253852 A1 | 9/2017 | Bayer et al. |
| 2018/0014468 A1 | 1/2018 | Ross et al. |
| 2018/0148682 A1 | 5/2018 | Ross et al. |
| 2018/0282529 A1 | 10/2018 | Kaplan-Bie |
| 2018/0368337 A1 | 12/2018 | McIntyre et al. |
| 2019/0059431 A1 | 2/2019 | Kozubal et al. |
| 2019/0090436 A1 | 3/2019 | Betts et al. |
| 2019/0284307 A1 | 9/2019 | Chase et al. |
| 2019/0322997 A1 | 10/2019 | Schaak |
| 2019/0330668 A1 | 10/2019 | Kozubal et al. |
| 2019/0338240 A1 | 11/2019 | Carlton et al. |
| 2019/0357454 A1 | 11/2019 | Mueller et al. |
| 2019/0359931 A1 | 11/2019 | Mueller et al. |
| 2019/0390156 A1 | 12/2019 | Bayer et al. |
| 2020/0024577 A1 | 1/2020 | Carlton et al. |
| 2020/0025672 A1 | 1/2020 | Scullin et al. |
| 2020/0055274 A1 | 2/2020 | Bayer et al. |
| 2020/0095535 A1 | 3/2020 | Kozubal et al. |
| 2020/0102530 A1 | 4/2020 | Winiski et al. |
| 2020/0146224 A1 | 5/2020 | Kaplan-Bie et al. |
| 2020/0157506 A1 | 5/2020 | Bayer et al. |
| 2020/0196541 A1 | 6/2020 | Ross et al. |
| 2020/0208097 A1 | 7/2020 | Winiski |
| 2020/0239830 A1 | 7/2020 | O'Brien et al. |
| 2020/0255794 A1 | 8/2020 | Amstislavski et al. |
| 2020/0268031 A1 | 8/2020 | Macur et al. |
| 2020/0270559 A1 | 8/2020 | Macur et al. |
| 2020/0392341 A1 | 12/2020 | Smith et al. |
| 2021/0017486 A1 | 1/2021 | Kozubal et al. |
| 2021/0127601 A9 | 5/2021 | Kaplan-Bie et al. |
| 2021/0348117 A9 | 11/2021 | Winiski |
| 2021/0401019 A1 | 12/2021 | Bayer et al. |
| 2022/0025318 A1 | 1/2022 | Gandia et al. |
| 2022/0142907 A1 | 5/2022 | Bayer et al. |
| 2022/0240557 A1 | 8/2022 | Kawabata et al. |
| 2022/0290199 A1 | 9/2022 | Greetham et al. |
| 2022/0295825 A1 | 9/2022 | Ghotra et al. |
| 2022/0298470 A1 | 9/2022 | Sayed et al. |
| 2022/0315881 A1 | 10/2022 | Macur |
| 2022/0333055 A1 | 10/2022 | Winiski et al. |
| 2022/0354068 A1 | 11/2022 | Carlton et al. |
| 2022/0354152 A1 | 11/2022 | Winiski et al. |
| 2022/0361424 A1 | 11/2022 | Mueller et al. |
| 2022/0386666 A1 | 12/2022 | Kawabata et al. |
| 2022/0396052 A9 | 12/2022 | Bayer et al. |
| 2023/0013465 A1 | 1/2023 | Kaplan-Bie et al. |
| 2023/0016412 A1 | 1/2023 | Perry |
| 2023/0024708 A1 | 1/2023 | Kaplan-Bie et al. |

(56) References Cited

U.S. PATENT DOCUMENTS

| | | | |
|---|---|---|---|
| 2023/0056666 A1 | 2/2023 | Winiski et al. | |
| 2023/0219265 A1 | 7/2023 | McIntyre et al. | |

FOREIGN PATENT DOCUMENTS

| | | |
|---|---|---|
| CN | 1358413 A | 7/2002 |
| CN | 1732887 A | 2/2006 |
| CN | 101248869 A | 8/2008 |
| CN | 101653081 A | 2/2010 |
| CN | 101743854 B | 2/2013 |
| CN | 103146585 A | 6/2013 |
| CN | 101892163 B | 7/2013 |
| CN | 103283482 B | 7/2014 |
| CN | 103396954 B | 11/2014 |
| CN | 104025909 B | 5/2016 |
| CN | 105961035 A | 9/2016 |
| CN | 106380166 A | 2/2017 |
| CN | 106635825 A | 5/2017 |
| CN | 106947702 A | 7/2017 |
| CN | 108249037 A | 7/2018 |
| CN | 108753624 A | 11/2018 |
| CN | 108934760 A | 12/2018 |
| CN | 109897394 A | 6/2019 |
| CN | 106613359 B | 1/2020 |
| CN | 111066577 A | 4/2020 |
| CN | 112225326 A | 1/2021 |
| CN | 112442449 A | 3/2021 |
| CN | 113501994 A | 10/2021 |
| CN | 108753625 B | 11/2021 |
| CN | 113692913 A | 11/2021 |
| CN | 114175968 A | 3/2022 |
| CN | 216106969 U | 3/2022 |
| CN | 114617025 A | 6/2022 |
| CN | 111990171 B | 7/2022 |
| CN | 115104479 A | 9/2022 |
| CN | 115181679 A | 10/2022 |
| EP | 0226292 A1 | 6/1987 |
| EP | 1312547 A1 | 5/2003 |
| EP | 2677030 A1 | 12/2013 |
| EP | 2735318 A1 | 5/2014 |
| EP | 2835058 A1 | 2/2015 |
| EP | 2875805 A1 | 5/2015 |
| EP | 2878340 A1 | 6/2015 |
| EP | 2485779 B1 | 2/2018 |
| EP | 3292769 A1 | 3/2018 |
| ES | 2497415 B1 | 4/2015 |
| FR | 3006693 A1 | 12/2014 |
| FR | 3071507 A1 | 3/2019 |
| GB | 142800 A | 1/1921 |
| GB | 1525484 A | 9/1978 |
| GB | 2032456 A | 5/1980 |
| GB | 2165865 A | 4/1986 |
| IN | 358266 B | 7/2020 |
| IN | 202111003691 A | 2/2021 |
| IN | 202141024595 A | 7/2021 |
| IN | 202031032279 A | 2/2022 |
| JP | S52066679 A | 6/1977 |
| JP | S55048388 A | 4/1980 |
| JP | H03234889 A | 10/1991 |
| JP | H049316 A | 1/1992 |
| JP | 2002104988 A | 4/2002 |
| JP | 2003526353 A | 9/2003 |
| JP | 2011130766 A | 7/2011 |
| JP | 2016512699 A | 5/2016 |
| JP | 6111510 B1 | 4/2017 |
| JP | 2023002897 A | 1/2023 |
| KR | 20050001175 A | 1/2005 |
| KR | 101569282 B1 | 11/2015 |
| KR | 101619664 B1 | 5/2016 |
| KR | 101851655 B1 | 4/2018 |
| KR | 102256335 B1 | 5/2021 |
| KR | 1020220138955 A | 10/2022 |
| KR | 102463058 B1 | 11/2022 |
| KR | 1020220163083 A | 12/2022 |
| KR | 1020220163084 A | 12/2022 |
| MX | 2017016725 A | 6/2019 |
| MY | 163845 A | 10/2017 |
| RU | 2716106 C1 | 3/2020 |
| WO | WO 1992/013960 | 8/1992 |
| WO | WO 1998/052403 | 11/1998 |
| WO | WO 1999/024555 | 5/1999 |
| WO | WO 2001/087045 | 11/2001 |
| WO | WO 2002/019798 | 3/2002 |
| WO | WO 2003/089506 | 10/2003 |
| WO | WO 2004/111181 | 12/2004 |
| WO | WO 2005/023323 | 3/2005 |
| WO | WO 2005/067977 | 7/2005 |
| WO | WO 2007/031129 | 3/2007 |
| WO | WO 2007/139321 | 12/2007 |
| WO | WO 2008/025122 | 3/2008 |
| WO | WO 2008/073489 | 6/2008 |
| WO | WO 2010/005476 | 1/2010 |
| WO | WO 2012/122092 | 9/2012 |
| WO | WO 2012/148995 | 11/2012 |
| WO | WO 2014/039938 | 3/2014 |
| WO | WO 2014/110539 | 7/2014 |
| WO | WO 2014/195641 | 12/2014 |
| WO | WO 2015/024751 | 2/2015 |
| WO | WO 2016/149002 | 9/2016 |
| WO | WO 2017/056059 | 4/2017 |
| WO | WO 2017/120342 | 7/2017 |
| WO | WO 2017/125602 A1 | 7/2017 |
| WO | WO 2017/132523 | 8/2017 |
| WO | WO 2017/136950 | 8/2017 |
| WO | WO 2017/151684 | 9/2017 |
| WO | WO 2017/205750 | 11/2017 |
| WO | WO 2018/011805 | 1/2018 |
| WO | WO 2018/014004 | 1/2018 |
| WO | WO 2018/064968 | 4/2018 |
| WO | WO 2018/183735 | 10/2018 |
| WO | WO 2018/189738 | 10/2018 |
| WO | WO 2019/046480 | 3/2019 |
| WO | WO 2019/099474 | 5/2019 |
| WO | WO 2019/178406 | 9/2019 |
| WO | WO 2019/217175 | 11/2019 |
| WO | WO 2019/226823 | 11/2019 |
| WO | WO 2019/237059 | 12/2019 |
| WO | WO 2019/246636 | 12/2019 |
| WO | WO 2020/023450 | 1/2020 |
| WO | WO 2020/072140 | 4/2020 |
| WO | WO 2020/082043 | 4/2020 |
| WO | WO 2020/082044 | 4/2020 |
| WO | WO 2020/102552 | 5/2020 |
| WO | WO 2020/106743 | 5/2020 |
| WO | WO 2020/176758 | 9/2020 |
| WO | WO 2020/186068 | 9/2020 |
| WO | WO 2020/186169 | 9/2020 |
| WO | WO 2020/237201 | 11/2020 |
| WO | WO 2021/092051 | 5/2021 |
| WO | WO 2021/144603 | 7/2021 |
| WO | WO 2022/079452 | 4/2022 |
| WO | WO 2022/091089 | 5/2022 |
| WO | WO 2022/135757 | 6/2022 |
| WO | WO 2022/157326 | 7/2022 |
| WO | WO 2022/189600 | 9/2022 |
| WO | WO 2022/195617 | 9/2022 |
| WO | WO 2022/200049 | 9/2022 |
| WO | WO 2022/212945 | 10/2022 |
| WO | WO 2022/265498 | 12/2022 |

OTHER PUBLICATIONS

Guan, C., Cui, W., Cheng, J et al. Construction and development of an auto-regulatory gene expression system in Bacillus subtilis . Microb Cell Fact 14, 150 (2015). https://doi.org/10.1186/s12934-015-0341-2.*

"Soil" according to Wikipedia, 51 pages of PDF retrieved from Wikipedia on Sep. 14, 2022.*

"Compost" according to Wikipedia, 21 pages of PDF retrieved from Wikipedia on Sep. 14, 2022.*

Sansinenea et al., Biotechnol Lett, 2011, vol. 33, p. 1532-1538.*

(56) References Cited

OTHER PUBLICATIONS

PubMLST (Public databases for molecular typing and microbial genome diversity), information on isolate Bacillus subtilis ATCC 6051, 1 page of PDF, retrieved from PubMLST on Sep. 15, 2022.*
Abbadi et al., "Immunocytochemical identification and localization of lipase in cells of the mycelium of Penicillium cyclopium variety", Appl Microbial Biotechnol (1995) 42: 923-930.
Ando et al., "Cosmetic material for skin whitening—contains mushroom mycelium cultured matter and e.g. ginseng extract, chondroitin sodium sulphate and/or hyaluronic acid", WPI/Thomson (Jan. 14, 1992), 1992(8): Accession #1992-062018; Abstract of JP4009316A; in 9 pages.
Antinori et al., "Advanced mycelium materials as potential self-growing biomedical scaffolds." Scientific reports (2021) 11(1): 1-14.
Attias et al., "Biofabrication of Nanocellulose-Mycelium Hybrid Materials", Adv Sustainable Syst. (2020) 5(2): 2000196 in 12 pages; Supporting Information in 7 pages.
Borrás et al., "Trametes versicolor pellets production: Low-cost medium and scale-up", Biochem Eng J. (2008) 42(1): 61-66.
Collins English Dictionary, "Cavity", Definition; retrieved on Nov. 8, 2021; 1 page.
Green et al., "Mechanical Properties of Wood", Forest Products Laboratory, 1999. in Wood Handbook—Wood as an engineering material. Gen Tech. Rep. FPL-GTR-113, Chapter 4 in 46 pages.
Hidayat et al., "Characterization of polylactic acid (PLA)/kenaf composite degradation by immobilized mycelia of Pleurotus ostreatus". Inter Biodeter Biodegrad. (2012) 71: 50-54.
Holt et al. "Fungal mycelium and cotton plant materials in the manufacture of biodegradable molded packaging material: Evaluation study of select blends of cotton byproducts." J Biobased Mater Bioenergy (2012) 6(4): 431-439.
Jiang et al., "Manufacturing of Natural Composites with a Mycelium Binder and Vacuum-infused Vegetable Oil-based Resins", Poster dated May 2014; 1 page.
Jiang et al., "Vacuum Infusion of Mycelium-Bound Biocomposite Preforms with Natural Resins", CAMX ExpoConference Proceedings, Oct. 13-16, 2014, 13 pages.
Jiang et al., "Bioresin Infused then Cured Mycelium-based Sandwich-structure Biocomposites: Resin Transfer Molding (RTM) Process, Flexural Properties, and Simulation." J Cleaner Production (2019) 207: 123-135.
Jones et al., "Mycelim Composites: A Review of Engineering Characteristics and Growth Kinetics", J Bionanoscience (2017) 11(4): 241-257.
Jones et al., "Waste-derived Low-cost Mycelium Composite Construction Materials with Improved Fire Safety", FAM (Fire and Materials) (2018) 42(7): 816-825.
Jones et al., Chitin-chitosan Thin Films from Microbiologically Upcycled Agricultural By-products. In 13th International Conference on the Mechanical Behavious of Materials, Melbourne, Australia (Jun. 2019) p. 66; in 7 pages.
Kuhn et al., [Eds.] Cell Walls and Membranes in Fungi—An Introduction (Abstract) in Biochemistry of Cell Walls and Membranes in Fungi, Chapter 1, Springer Verlag Berlin/Heidelberg 1990, 2 pages.
Merriam-Webster, "desiccated" (Adj.) Definition; downloaded on Nov. 8, 2021; 1 page.
Meyer et al., "Comparison of the Technical Performance of Leather, Artificial Leather, and Trendy Alternatives." Coatings (Feb. 2021) 11(2): 226; 14 pages.
Pathway-27, "Beta-glucan", Aug. 2012, retrieved from http://http://www.pathway27.eu/topstory/beta-glucan/ on Oct. 7, 2021 in 2 pages.
Vetchinkina et al., "Bioreduction of Gold (III) Ions from Hydrogen Tetrachloaurate . . . " Scientific Practical J Health Life Sciences No. 4, ISSN 22188-2268. (2013) pp. 51-56.
Wang et al., "Chemical and structural factors influencing enzymatic saccharification of wood from aspen, birch and spruce". Biomass Bioengin. (2018) 109: 125-134.
Williams, J. "Growth Industry", Financial Times Jan. 12, 2019 (Mogu—Radical by Nature); download from URL <: https://mogu.bio/growth-industry-financial-times-uk-article/> in 1 page.
Wösten et al., "How a fungus escapes the water to grow into the air", Current Biology. (1999) 9(2): 85-88.
Wösten et al., "Growing Fungi Structures in Space", ACT Research Category/Space Architecture; Noordwijk, The Netherlands (Oct. 15, 2018) in 17 pages.
Zeng Z., "Cosmetic composition for cleaning skin, comprises glossy ganoderma spores and collagens, content of glossy ganoderma spores in composition and content of collagens in composition", WPI/Thomson (Feb. 5, 2006) 7: Accession #2007-057767; Abstract of CN1732887A; in 11 pages.
Ziegler et al., "Evaluation of Physico-mechanical Properties of Mycelium Reinforced Green Biocomposites Made from Cellulosic Fibers", Appl Engin Agricult. (2016) 32(6): 931 -938.
PhpBB Shopsmith Forums, "Cracks in wide paneling boards", Excerpt from Oct. 28, 2017, downloaded from URL <https://www.shopsmith.com/ss_forum/viewtopic.php?p=214601>; 2 pages.
Antón et al., "PimM, a PAS Domain Positive Regulator of Pimaricin Biosynthesis in Streptomyces natalensis." Microbiol. (2007) 153: 3174-3183.
Appels et al., "Hydrophobin gene deletion and environmental growth conditions impact mechanical properties of mycelium by affecting the density of the material." Scientific Reports (2018) 8(1): 1-7.
Arshad et al., "Tissue engineering approaches to develop cultured meat from cells: a mini review." Cogent Food & Agriculture (2017) 3(1): 1320814 in 11 pages.
Belardinelli et al., "Actions of Adenosine and lsoproterenol on Isolated Mammalian Ventricular Myocytes." Circulation Res. (1983) 53(3): 287-297.
Belay et al., "Preparation and Characterization of Graphene-agar and Graphene Oxide-agar Composites." JOAPS (2017) 134(33): 45085.
Bormann et al., "Characterization of a Novel, Antifungal, Chitin-binding Protein from Streptomyces Tendae Tü901 that Interferes with Growth Polarity." J Bacter. (1999) 181(24): 7421-7429.
Bružauskaite et al., "Scaffolds and Cells for Tissue Regernation: Different Scaffold Pore Sizes—Different Cell Effects." Cytotechnology (2016) 68(3): 355-369.
Byrd, "Clean meat's path to your dinner plate", The Good Food Institute, website accessed Nov. 14, 2018, https://www.gfi.org/clean-meats-path-to-commercialization; 11 pages.
Cerimi et al., "Fungi as source for new bio-based materials: a patent review", Fungal Biol Biotechnol. (2019) 6: 17; 10 pgs.
Chi et al., "Can Co-culturing of Two White-rot Fungi Increase Lignin Degradation and the Production of Lignin-degrading Enzymes?" Inter'l Biodeter Biodegrad. (2007) 59(1): 32-39.
Glowacki et al., "Bioconjugation of Hydrogen-bonded Organic Semiconductors with Functional Proteins." J Mate Chem. C (2015) 3(25): 6554-6564.
Greetham et al., "Pheotypic characterisation of Saccharomyces sensu stricto to Inhibitory Compounds Released During the Deconstruction of Lignocellulosic Material." 3th International Congress on Yeasts, ICY 2012, Aug. 26-30, Madison, USA; 1 page.
Griffin et al., "Regulation of macromolecular synthesis, colony development and specific growth rate of Achlya bisexualis during balanced growth". J General Microbiol. (1974) 80(2): 381-388.
Growers Supply. "Horticultural Coarse Perlite—4 Cubic Fee—Growers Supply". URL: https://growerssupply.com; Growers Supply 2012; www.growerssupply.com/farm/supplies/prod1:gs_growing_mediums:pg111049.html; downloaded Dec. 14, 2020 in 3 pages.
Haneef et al., "Advanced Materials from Fungal Mycelium: Fabrication and Tuning of Physical Properties", Scientific Reports 7(1): 1-11; DOI: 10.1038/srep41292, Jan. 24, 2017.
Heisig et al., USGS, "Ground-Water Resources of the Clifton Park Area, Saratoga County, New York", 2002, retrieved from the internet (Oct. 15, 2016): http://ny.water.usgs.gov/pubs/wri/wri014104/wrir01-4104.pdf; 27 pages.
Home Depot "Miracle Gro® Perlite Mix", retrieved from the internet: http://homedepot.com/p/Miracle-Gro-8-pt-Perlite-MiX-74278430/204502291; 2 pages.

(56) References Cited

OTHER PUBLICATIONS

Home Depot "Pennington—Fast Acting Gypsum", retrieved from the internet: http://homedepot.com/p/Miracle-Gro-8-pt-Perlite-MiX-74278430/204502291; 2 pages.
Howden et al., "The effects of breathing 5% CO2 on human cardiovascular responses and tolerance to orthostatic stress". Exper. Physiol. (2004) 89(4): 465-471.
Hüttner et al., "Recent advances in the intellectual property landscape of filamentous fungi", Fungal Bil Biotechnol. (2020) 7:16; 17 pgs.
Instructables, How to Grow Oyster Mushroom Spawn (Low Tech), retrieved from the internet Aug. 19, 2018: http://www.instructables.com/id/1-How-to-Grow-Oyster-Mushroom-Spawn-Low-Tech/; 17 pages.
Jones et al., "Leather-like material biofabrication using fungi", Nature Sustainability (2020) https://doi.org/10.1038/s41893-020-00606-1, Sep. 7, 2020.
Kemppainen et al., "Transformation of the Mycorrhizal Fungus Laccaria Bicolor using Agrobacterium tumefaciens." Bioengin Bugs (2011) 2(1): 38-44.
Kim et al., "Current Technologies and Related Issues for Mushroom Transformation." Mycobiology (2015) 43(1): 1-8.
Kotlarewski et al., "Mechanical Properties of Papua New Guinea Balsa Wood." European J Wood Wood Products (2016) 74(1): 83-89.
Kües, U., "Life History and Development Processes in the Basidiomycete Coprinus Cinereus." Micro Molecular Biol Rev. (2000) 64(2): 316-353.
Kuhar et al., by Ingredi Potassium Sorbate vs Campden Tablets in Wine Making; Jun. 4, 2018. [online]; Retrieved from the Internet <URL: https://ingredi.com/blog/potassium-sorbate-vs-campden-tables-in-wine-making/>; 2 pages.
McPherson et al., "Dissolvable Antibiotic Beads in Treatment of Periprosthetic Joint Infection and Revision Arthroplasty: The Use of Synthetic Pure Calcium Sulfate (Stimulan®) Impregnated with Vancomycin & Tobramycin." Reconstructive Review (2013) 3(1) 12 pages.
Merrlam-Webster, "Chamber" dictionary definition; https://www.merriam-webster.com/dictionary accessed Jul. 10, 2017; in 4 Pages.
Merriam-Webster, "pack" Thesaurus definition; https://www.merriam-webster.com/thesaurus; synonyms accessed Aug. 19, 2019; in 10 Pages.
Michielse et al., "Agrobacterium-mediated Transformation of the Filamentous Fungus Aspergillus Awamori." Nature Protocols (2008) 3(10): 1671-1678.
Mitchell et al., [Eds.] "Solid-State Fermentation Bioreactors." Springer Verlag, Berlin/Heidelberg (2006); TOC in 12 Pages.
Moore D., "Fungal Morphogenesis." Cambridge University Press, Cambridge, UK; (1998) TOC in 8 Pages.
Moore D., "Tolerance of lmprecision in Fungal Morphogenesis." In Proceedings of the 4th Meeting on the Genetics and Cellular Biology of Basidiomycetes (Mar. 1998) pp. 13-19.
Naknean et al., "Factors Affecting Retention and Release of Flavor Compounds in Food Carbohydrates." Inter'l Food Res J. (2010) 17(1): 23-34.
Newaz et al., "Characterization of Balsa Wood Mechanical Properties Required for Continuum Damage Mechanics Analysis." Proceedings of the Institution of Mechanical Engineers, Part L: Journal of Materials: Design and Applications (2016) 230(1): 206-218.
Nussinovitch "Polymer Macro-and Micro-Gel Beads: Fundamentals and Applications", DOI 10.1007/978-1-4419-6618_2, Springer Science & Business Media LLC (2010) TOC in 8 Pages.
Paz et al., "One Step Contruction of Agrobacterium-Recombination-ready-plasmids (OSCAR): An Efficient and Robust Tool for ATMT Based Gene Deletion Construction in Fungi." Fungal Gen Biol. (2011) 48(7): 677-684.
Peksen et al., "Favourable Culture Conditions for mycelial growth of Hydnum repandum, a medicinal mushroom." African Journal of Traditional, Complementary and Alternative Medicines (2013) 10(6): 431-434.
Pinterest Fungus Objects: Alaska and Canada; Collection by Deborah Tear Haynes, downloaded from URL <https://www.pinterest.com/deborahtear/fungi-textile-ketchikan-alaska/>;1 page, 2020.
Ross, P., "Pure Culture" 1997-Present; URL: <http://billhoss.phpwebhosting.com/ross/index.php?kind>; downloaded Dec. 14, 2016 in 11 pages.
Schaner et al., "Decellularized Vein as a Potential Scaffold for Vascular Tissue Engineering." J Vascular Surg. (2004) 40(1): 146-153.
Schuurman J., "Unique agar Pearls." YouTube video; Feb. 16, 2012, <https://www.youtube.com/watch?v=8GgTTOHETPQ>; 1 page.
Seamon K.B., "Forskolin: Unique Diterpene Activator of Adenylate Cyclase in Membranes and in Intact Cells." PNAS (1981) 78(6): 3363-3367.
Stamets, "Growing Gourmet and Medicinal Mushrooms", Chapter 21 ; p. 363, 1993.
Stanev et al., "Open Cell Metallic Porous Materials Obtained Through Space Holders. Part I: Production Methods, A Review". JMSE (2016) 139(5): 21 pages.
Stephens et al., "Bringing Cultured Meat to Market: Technical, Socio-political, and Regulatory Challenges in Cellular Agriculture." Trends in Food Science & Technology (2018) 78: 155-166.
Timberpress—"How Do Mushrooms Grow So Quickly.", downloaded from the internet: www.timberpress.com/blog/2017/01/how-do-mushrooms-grow-so-quickly, download Feb. 27, 2018 in 7 Pages.
Wikipedia, "Water gel (plain)", Wikipedia Contributors downloaded Aug. 21, 2017 in 1 Page.
Xiao et al., "A Water-soluble Core Material for Manufacturing Hollow Composite Sections." Comp. Structures (2017) 182: 380-390.
Zadrazil et al., "Influence of CO2 Concentration on the Mycelium Growth of Three Pleurotus Species", European J. Appl. Microbiol., vol. 1, pp. 327-335 (1975).
Agnese et al., "Investigating the Influence of Various Plasticizers on the Properties of Isolated Films of Polyvinyl Acetat". The 37th Annual meeting and Exposition of the Controlled Release Society, Jul. 2010, Portland, OR U.S.A.
Amsellem et al., "Long-term preservation of viable mycelia of two mycoherbicidal organisms". Crop Protection (1999) 18: 643-649.
Angelini et al., "Effect of antimicrobial activity of Melaleuca alternifolia essential oil on antagonistic potential of Pleurotus species against Trichoderma harzianum in dual culture." World J Microbiol Biotech. (2008) 24(2): 197-202.
Ashiuchi et al., "Isolation of Bacillus subtilis (chungkookjang), a poly-gamma-glutamate producer with high genetic competence". Appl Microbiol Biotechnol. (2011) 57: 764-769.
Bajaj et al., "Poly (glutamic acid)—An emerging biopolymer of commercial interest". Bioresource Tech. (2011) 102(10): 5551-5561.
Baysal et al., "Cultivation of oyster mushroom on waste paper with some added supplementary materials". Biosource Technology (2003) 89: 95-97.
Begum et al., "Bioconversion and saccharification of some lignocellulosic wastes by Aspergillus oryzae ITCC-4857.01 for fermentable sugar production". Elect J Biotech. (2011) (14)5: 3 in 8 pages.
Binder et al., "Phylogenetic and phylogenomic overview of the Polyporales". Mycologia (Nov.-Dec. 2013) 105(6): 1350-1373.
Blanchette et al., "Fungal mycelial mats used as textile by indigenous people of North America", Mycologia (Feb. 20, 2021) pp. 1-7.
Booth et al., "Potential of a dried mycelium formulation of an indigenous strain of Metarhizium anisopliae against subterranean pests of cranberry." Biocontrol Science and Technology (2000) 10: 659-668.
Bowman et al., "The structure and synthesis of the fungal cell wall". Bioassays (2006) 28(8): 799-808.
Chai et al., "β-Glucan Synthase Gene Overexpression and β-Glucans Overproduction in Pleurotus ostreatus Using Promoter Swapping". PLoS ONE (2013) 8(4): e61693 in 7 pages.
Chaudhary et al., "Understanding rice hull ash as fillers in polymers: a review". Silicon Chemistry (2002) 1:281-289.

(56) References Cited

OTHER PUBLICATIONS

Collins English Dictionary, "Mould", retrieved from http://collinsdictionary.com/dictionary/english/mould, archived on Apr. 8, 2015, 3 pages.
Dias et al., "Synthesis and characterization of chitosan-polyvinyl alcohol-bioactive glass hybrid membranes". Biomatter (2011) 1(1): 114-119.
Elleuche et. al., "Carbonic anhydrases in fungi". Microbiology (2010) 156: 23-29.
Elsacker et al., "Growing living and multifunctional mycelium composites for large-scale formwork applications using robotic abrasive wire-cutting", Construction Bldg Mater. (2021) 283: 122732 in 16 pages.
Fleet G.H., "Cell walls". in The Yeasts, by Rose et al. [Eds.] 2nd Edition. vol. 4. London: Academic Press. (1991) pp. 199-277.
Frandsen R.J.N., "A guide to binary vectors and strategies for targeted genome modification in fungi using Agrobacterium tumefaciens-mediated transformation". J Microbiol Methods (2011) 87: 247-262.
Gardening KnowHow, Perlite Soil Info: Learn About Perlite Potting Soil, online at www.gardeningknowhow.com/garden-how-to/soil-fertilizers/perlite-potting-soil.htm downloaded on Dec. 16, 2015., 3 pages.
Goodell et al., "Fungal Decay of Wood: Soft Rot-Brown Rot-white Rot". In Development of Commercial Wood Preservatives; Schultz et al. [Ed.]ACS Symposium Series; American Chemical Society, Washington, D.C. (2008), Chapter 2, pp. 9-31.
Google Report, Complete colonization substrate mushroom (2 pages) Jan. 30, 2018., 2 pages.
Google Dictionary Definition "Composite", downloaded on Nov. 21, 2018; 1 page.
Gourmet Mushroom, Inc., "What is Mushroom?"—Mushroom Facts Mushroom Information—Educational & Science Projects (2004). Downloaded from www.gmushrooms.com, on Nov. 27, 2017; 5 pages.
Grant, James. J.—"An investigation of the airflow in mushroom growing structures, the development of an improved, three-dimensional solution technique for fluid flow and its evaluation for the modelling of mushroom growing structures", Doctoral Thesis Sep. 2002; 326 pages.
Heinzkill et al., "Characterization of laccases and peroxidases from wood-rotting fungi (family Coprinaceae)." Appl Environ Microbiol. (1998) 64: 1601-1606.
Horton et al., "Regulation of Dikaryon-EXpressed Genes by FRT1 in the Basidiomycete Schizophyllum commune". Fungal Genet Biol. (1999) 26(1): 33-47.
Hyde et al., "The amazing potential of fungi: 50 ways we can exploit fungi industrially". Fungal Diversity (2019) 97(1): 1-136.
Kamzolkina et al., "Micromorphological features of Pleurotus pulmonarius (Fr.) Ouel. and P. ostreaturs (Jacq.) P. Kumm. Strains in pure and binary culture with yeasts". Tsitologiia (2006) 48(2): 153-160.
Kerem et al., "Effect of Mananese on Lignin Degradation by Pleurotus ostreatus during Solid-State Fermentation". Applied and Environmental Microbiology (1993) 59(12): 4115-4120.
Kilaru et al., "Investigating dominant selection markers for Coprinopsis cinerea: a carboxin resistance system and re-evaluation of hygromycin and phleomycin resistance vectors". Curr Genet. (2009) 55: 543-550.
Kück et al., "New tools for the genetic manipulation of filamentous fungi". Appl Microbiol Biotechnol. (2010) 86: 51-62.
Kuo, 2005-2006. Glossary of Mycological Terms. Mushroom Expert. Com., pp. 1-13; downloaded from http://www.mushroomexpert.com/glossary.html (May 8, 2015).
Li et al., "Preparation and Characterization of Homogeneous Hydroxyapatite/Chitosan Composite Scaffolds via In-Situ Hydration". J Biomaterials Nanobiotech. (2010) 1: 42-49.
Luo et al., "Coprinus comatus: a basidiomycete fungus forms novel spiny structures and infects nematode." Mycologia (2004) 96(6): 1218-1225.
Mushroom Growers' Handbook 1, "Oyster Mushroom Cultivation". Part II, Chapter 5, (2005) pp. 75-85.
Mushroom Growers' Handbook 2, "Shiitake Bag Cultivation", Part I Shiitake. Published by Mush World (2005) Chapter 4, pp. 73-90 and pp. 105-109.
Norvell L., Fungi Biology. Encyclopedia.(2002); 2 pages.
Novoselova et al., "Cocultivation of Pleurotus ostreatus (Jacq.) P. Kumm. with yeasts". Moscow University Biol Sciences Bulletin (2011) 66(3): 102-105.
Peng et al., "Microbial biodegradation of polyaromatic hydrocarbons". FEMS Microbiol Rev. (2008) 32:927-955.
Perez et al., "Myxococcus xanthus induces actinorhodin overproduction and aerial mycelium formation by Streptomyces coelicolor. "Microbial Biotech. (2011) 4(2): 175-183.
Philippoussis et al., "Production of Mushrooms Using Agro-Industrial Residues as Substrates", in Biotechnology for Agro-Industrial Residues, Chapter 9, (2009) pp. 163-187.
Poppe J., Mushroom Growers' Handbook 1, 2004, Part II. Chapter 5, "Substrate", pp. 80-81.
Pompei et al., "The Use of Olive Milling Waste-Water for the Culture of Mushrooms on Perlite". Acta Horticulturae (1994) 361:179-185.
Rai et al., "Production of Edible Fungi", in Fungal Biotechnology in Agricultural, Food, and Environmental Applications, D.K. Arora [Ed.], Marcel Dekker, Inc, (2003), Chapter 21, pp. 383-404.
Royse et al., "Influence of substrate wood-chip particle size on shiitake (*Lentinula edodes*) yield". Bioresource Tehnology (2001) 76(3): 229-233.
Sapak et al., "Effect of endophytic bacteria on growth and suppression of Tganoderma infection in oil palm". Int J Agric Biol. (2008) 10(2): 127-132.
Schirp et al., "Production and characterization of natural fiber-reinforced thermoplastic composites using wheat straw modified with the fungus Pleurotus ostreatus". J Appl. Polym Sci. (2006) 102: 5191-5201.
Scholtmeijer et al., "Effect of introns and AT-rich sequences on expression of the bacterial hygromycin B resistance gene in the basidiomycete Schizophyllum commune". Appl Environ Microbiol. (2001) 67(1): 481-483.
Science Daily, May 7, 2007, retrieved from the Internet; http://www.sciencedaily.com/releases/2007/05/070506085628.htm., 3 pages.
Sinotech et al., (2015): retrieved from the Internet http://www.sinotech.com/compressionAndTransferMolding.html., 4 pages.
Slater, M. "Young SoRo Entrepreneur Develops Environmentally Friendly Insulation." The Herald of Randolph. Jun. 21, 2007, pp. 1-2.
Staib et al., "Differential expression of the NRG1 repressor controls species-specific regulation of chlamydospore development in Candida albicans and Candida dubliniensis." Molecular Microbiol. (2005) 55(2): 637-652.
Stamets P., "Mycelium Running". Ten Speed Press (2005); pp. 18, 56, 58, 59, 85, 149, 157, 160 and 291 only.
Sundari et al., "Freeze-drying vegetative mycelium of Laccaria fraterna and its subsequent regeneration". Biotechnology Techniques (1999) 13: 491-495.
Tartar et al., "Differential expression of chitin synthase (CHS) and glucan synthase (FKS) genes correlates with the formation of a modified, thinner cell wall in in vivo-produced Beauveria bassiana cells." Mycopathologia (2005) 160(4): 303-314.
Téllez-Jurado et al., "Expression of a heterologous laccase by Aspergillus niger cultured by solid-state and submerged fermentations." Enzyme Microbial Tech. (2006) 38(5): 665-669.
Téllez-Téllez et al., "Growth and laccase production by Pleurotus ostreatus in submerged and solid-state fermentation." Appl Microbiol Biotechnol. (2008) 81 (4): 675-679.
Thomas et al., "Growing Orchids in Perlite". In Perlite Plant Guide, The Schundler Company 1951, pp. 1-6, downloaded from http://www.schundler.com/index.html, archived on May 11, 2015.
Ugalde U., "Autoregulatory Signals in Mycelial Fungi" in The Mycota: A Comprehensive Treatise on Fungi as Experimental Systems for Basic and Applied Research. K. Esser [Ed.] Springer Publisher, 2nd Edition (2006) Chapter 11; pp. 203-213.

(56) References Cited

OTHER PUBLICATIONS

Universal Oil Field, "Sawdust", downloaded from universaloilfield. org on Aug. 23, 2018, 4 pages.
Vara et al., "Cloning and expression of a puromycin N-acetyl transferase gene from Streptomyces alboniger in Streptomyces lividans and *Escherichia coli*". Gene (1985) 33(22): 197-206.
Visser et al., "Pseudoxylaria as stowaway of the fungus-growing termite nest: Interaction asymmetry between Pseudoxylaria, Termitomyces and free-living relatives". Fungal Ecology (2011) 4(5): 322-332.
Volk (2003) "Tom Volk's Fungus of the Month for Oct. 1998". This month's fungus is Pleurotus ostreatus; the Oyster mushroom, pp. 1-4, downloaded from http://botit.botany.wise.edu/toms_fungi/oct98.html on May 8, 2015.
Wang et al., "Influence of fungal elicitors on biosynthesis of natamycin by Streptomyces natalensis HW-2". Appl Microbiol Biothechnol. (2003) 97: 5527-5534.
Wikipedia, "Wood", downloaded on Nov. 26, 2018, 1 page.
Yang et al., "Medicinal Mushroom Ganoderma lucidum as a Potent Elicitor in Production of t-Resveratrol and t-Peceatannol in Peanut Calluses". J Agric Food Chem. (2010) 58(17): 9518-9522.
Zimin et al., "The MaSuRCA genome assembler". Bioinformatics (2013) 29(21): 2669-2677.
Bartnickl-Garcia, "Cell wall chemistry, morphogenesis, and taxonomy of fungi", Annual Review Microbiol. (1968) 22(1): 87-108.
Cha et al., "Biomimetic synthesis of ordered silica structures mediated by block copolypeptides". Nature (2000) 403(6767): 289-292.
Dugdale J. "This new surf company is making boards of mushrooms". Blog post—Jun. 25, 2015.
Halseide P., "Cutting brick the safe way". The Aberdeen Group (1988) Publication #M880354 in 2 pages.
Highland Woodworking, "Making Thin Lumber and Veneer Out of Ordinary Boards", Sales Website (2017) in 3 pages.
Holt et al., "Biobased Composition Boards Made from Cotton Gin and Guayule Wastes: Select Physical and Mechanical Properties", Int J Mater Prod Tech. (2009) 36: 104-114.
Islam et al., "Morphology and mechanics of fungal mycelium", Scientific Reports, (2017) 7(1): 1-12.
Kerem et al., "Chemically defined solid-state fermentation of Pleurotus Ostreatus". Enzyme Microbiol Tech. (1993) 15(9): 785-790.
Kokubo et al., "Ca,P-rich layer formed on high-strength bioactive glass-ceramic A-W". J Biomed Mater Res. (1990) 24(3): 331-343.
Koutsoukos et al., "Precipitation of calcium carbonate in aqueous solutions". J Chem Soc., Faraday Trans. 1, Physical Chemistry in Condensed Phases, (1984) 80(5): 1181-1192.
Lu et al., "Theoretical Analysis of Calcium Phosphate precipitation in simulated Body Fluid". Biomaterials (2005) 26(10): 1097-1108—Pre-Pub. Version by Hong Kong University of Science and Technology, Department of Mechanical Engineering, Kowloon; 34 pages.
Molvinger et al., "Porous chitosan-silica hybrid microspheres as a potential catalyst". Chem Mater. (2004) 16(17): 3367-3372.
Monmaturapoj et al., "Influence of preparation method on hydroxyapatite porous scaffolds". Bull Mater Sci. (2011) 34(7): 1733-1737.
Manoli et al., "Crystallization of calcite on chitin". J Cryst Growth, (1997) 182(1-2): 116-124.
Mushroom Source, "Aspen Wood Shavings for Mushroom Cultivation", Website (2015) in 2 pages.
National Institute of Health (NIH/NIBIB), "Tissue Engineering and Regenerative Medicine", Retrieved Sep. 24, 2018 from https://www.nibib.nih.gov/science-education/science-topics/tissue-engineering-and-regenerative-medicine in 13 pages.
Passauer U. et al., "Pilze in Hohlen" [Cave Mushrooms]. Denisia (2016) 37: 211-224.
Stewart B., "Concrete Fence Posts: Fact Sheet", Texas Agriculture Extension Service, Texas A & M University (1975) Article L-1368 in 4 pages.
Trlnci et al., "II. Unrestricted Growth of Fungal Mycelia", The Mycota—Growth, Differenciation and Sexuality by Wessels et al. [Eds], Springer, Berlin, Heidelberg, (1994) Chapter II: 175-193.

Udawatte et al., "Solidification of xonotlite fibers with chitosan by hydrothermal hot pressing". J Mater Sci. Lttrs. (2000) 45(6): 298-301.
University of Sydney, "Competition Between Fungi". Webpage, accessed Jul. 16, 2014—http://bugs.bio.usyd.edu.au/learning/resources/Mycology/Ecology/competition.shtml in 3 pages.
Varma et al., "Porous calcium phosphate coating over phosphorylated chitosan film by a biomimetic method". Biomaterials (1999) 20(9): 879-884.
Wagner A. "Mycelium Biking—Eco-Design at its Best", Master's Thesis at Lulea University of Technology (2016) in 92 pages.
Woller R. "The Pearl Oyster Mushroom", University of Wisconsin Website (2011) in 2 pages.
Wan-Mohtar et al., "The morphology of Ganoderma lucidum mycelium in a repeated-batch fermentation for exopolysaccharide production", Biotechnology Reports (2016) 11: 2-11.
Weaver et al., "The stomatopod dactyl club: a formidable damage-tolerant biological hammer". Science (2012) 336(6086): 1275-1280.
Yamasaki et al., "A hydrothermal hot-pressing method: Apparatus and Application". J Mater Sci Lttrs. (1986) 5(3): 355-356.
Zivanovlc et al., "Changes in Mushroom Texture and Cell Wall Composition Affected by Thermal Processing". J Food Service (2004) 69: 44-49.
Bandalan et al., "Inhibitory effect of garlic (*Allium sativum* L.) against bread mold and its influence on the quality of yeast-leavened bread", Int J Food Engineer. (Dec. 2018) 4(4): 256-262.
Bianchi et al., "Comparison between Allo-Kramer and Warner Bratzler Devices to Assess Rabbit Meat Tenderness", Italian J Animal Science (2007) 6(suppl): 749-751.
Boudaoud et al., "FibrilTool, an ImageJ plug-in to quantify fibrillar structures in rax microscopy images", Nature Protocols (2014) 9: 457-483.
Enrione et al., "Edible scaffolds based on non-mammalian biopolymers for Myoblast growth". Materials (Basel) (Dec. 2017) 10(12): 1404 in 15 pages.
Kumla et al., "Cultivation of Mushrooms and Their Lignocellulolytic Enzyme Production Through the Utilization of Agro-Industrial Waste". Molecules 2020 Jun;25(12): 2811 in 41 pages.
Miller R.K., "Quality Characteristics", in Muscle Foods: Meat Poultry and Seafood Technology, Kinsman et al. [eds], Springer Science & Media, (Mar. 2013) Chapter 11, 37 pages.
Ocde—Organisation for Economic Co-operation and Development, Environment, Health and Safety Publications Series on the Safety of Novel Foods and Feeds, No. 26, Consensus Document on Compositional Considerations for New Varieties of Oyster Mushroom [Pleurotus ostreatus]: Key Food and Feed Nutrients, Anti-nutrients and Toxicants; Paris November 2013, 42 pages.
Pacouette et al., "Simultaneous determination of chromium, selenium, and molybdenum in nutritional products by inductively coupled plasma/mass spectrometry: Single-laboratory validation", J of AOAC International (Jul. 2011) 94(4): 1240-1252.
Phiillips E., "Lignocellulose-degrading Microbes Give Plants New Life", American Soc Microb. (Mar. 25, 2022) 6 pages.
Roshita et al., "Effect of exposure to different colors light emitting diode on the yield and physical properties of grey and white oyster mushrooms", AIP Conference Proceedings (Nov. 2018) 2030(1): 020110 in 8 pages.
Voronin et al., "Carbon and Nitrogen Isotope Composition of the Wood of Pinus sylvestris, Betula pendula and Populus tremula". Paleonotal J., Dec. 2020;54(8): 819-824.
Zeigler et al., "The Origins of 168, W23, and other Bacillus subtilis Legacy Stains", J Bacter. (Nov. 2008) 190: 6983-6995.
Britannica, The Editors of Encyclopedia. "mold". Encyclopedia Britannica, Feb. 7, 2021, https://www.britannica.com/science/mold-fungus. 1 page.
Kim et al., "Effect of aeration and agitation on the production of mycelial biomass and exopolysaccharides in an enthomopahtogenic fungus *Paecilomyces sinclairlii*". Ltts Applied Microbiol. May 1, 2003;36(5):321-326.
Lumb et al., "Metal Chelating Tendencies of Glutamic and Aspartic Acids". J Phys Chem., Jul. 1953;57(7): 690-693.

(56) References Cited

OTHER PUBLICATIONS

Magyar C., "11 Smart uses for sawdust around your home & garden". Rural Sprout, published Oct. 26, 2020, 19 pages.

Mitcheson et al., "Cultured adult cardiac myocytes: Future applications, culture methods, morphological and electrophysiological properties". Cardiovasc Res. (1998) 39: 280-300.

Pang et al., "Facile fabrication of gradient density organic aerogel foams via density gradient centrifugation and UV curing in one-step", J Sol-Gel Sci Technol. (Nov. 2018) 85: 243-250.

Peter et al., "High Terpene Pines: Transforming existing and enabling new forest biorefineries". 2013; 1 page.

Silverman J., "Development and Testing of Mycelium-based Composite Materials for Shoe Sole Applications." Thesis Spring 2018; Retrieved from the Internet: URL: http://udspace.udel.edu/bitstream/handle/19716/23768/Silverman_udel_006M_13300.pdf?sequence=1&isAllowed=y; (Apr. 1, 2018); 99 pages.

Tapias et al., Decellularized scaffolds as a platform for bioengineered organs, Curr Opin Organ Transplant (Apr. 2014) 19(2): 145-152.

Yang et al., "Physical and mechanical properties of fungal mycelium-based biofoam", J Mater Civil Engin. (Jul. 2017) 29(7): 04017030 in 9 pages.

Hartl et al., "Fungal chitinases: diversity, mechanistic properties and biotechnological potential". Appl Microbiol Biotechnol. Jan. 2012;93: 533-543.

IFC Solutions. Natural Food Coloring. 2023; pp. 1-4.

Millipore Sigma Database Search "Chelators", 2023, pp. 1-4.

Wrona T., 10 Powerful Nutrients Found Only in Meat. Jun. 9, 2022. 20 pages.

ASTM International, "Standard Test Method for Tensile Properties of Plastics". Designation: D638-10, published Jun. 2010 in 16 pages.

Elsacker et al., "Mechanical, physical and chemical characterisation of mycelium-based composites with different types of lignocellulosic substrates". PLOS One. Jul. 22, 2019;14(7): e0213954 in 20 pages.

Elsoud et al., "Current trends in fungal biosynthesis of chitin and chitosan". Bull Nat'l Res Centre. Dec. 2019;43(1): 12 pages.

Fisher A., "Industrial-strength fungus—Densely packed rootlike fibers can do the job of Styrofoam, insulation and, yes, even bricks". TIME Feb. 8, 2010:1 page.

INSIDER Business, "How Mushrooms are Turned into Bacon and Styrofoam—World Wide Waste", Apr. 11, 2021; XP093055859; Retrieved from the Internet: URL:https://www.youtube.com/watch?v=uznX18wrdag&t=325s&ab_channel=InsiderBusiness [retrieved on Jun. 20, 2023] in 4 pages.

Kadirgamar S., "Company Uses Mushrooms to Grow Plastic Alternatives". Oct. 17, 2017; downloaded from https://daily.jstor.org/daily-author/skanda-kadirgamar/ in 5 pages.

Kumar, M.N.V.R., "A review of chitin and chitosan applications". React Function Polymers. Nov. 1, 2000;46(1):1-27.

\* cited by examiner

BIO-MANUFACTURING PROCESS

CROSS-REFERENCE TO RELATED APPLICATIONS

Any and all applications for which a foreign or domestic priority claim is identified in the Application Data Sheet as filed with the present application are hereby incorporated by reference under 37 CFR 1.57.

This is a Non-Provisional application and claims the priority benefit of U.S. Provisional Patent Application No. 62/649,175, filed Mar. 28, 2018, the full disclosure of which is incorporated herein by reference.

This invention relates to method a bio-manufacturing process. More particularly, this invention relates to method a bio-manufacturing process involving the development of a cohabitation platform incorporating reprogrammed (genetically engineered) bacterial and fungal components in order to improve existing processes of producing myceliated material.

As is known from U.S. Pat. No. 9,485,917, a composite material comprised of discrete particles and a network of interconnected mycelia cells bonding the discrete particles together can be made by inoculating a substrate of the discrete particles and a nutrient material with a preselected fungus. As described, the fungus digests the nutrient material over a period of time sufficient to grow hyphae and to allow the hyphae to form a network of interconnected mycelia cells through and around the discrete particles thereby bonding the discrete particles together to form a self-supporting composite material.

It has also been known to employ a bio-manufacturing process to make a composite material as described in U.S. Pat. No. 9,485,917 by leveraging domestic agricultural waste products, e.g. corn stalks, and inoculating these with various fungal species. The fungi utilize the agricultural substrate as the sole energy source, growing new cells (mycelia) that ramify throughout the material.

It has also been known from U.S. Pat. No. 10,125,347 to make a composite biomaterial that employs a binding organism, such as a filamentous fungi that produce mycelium, based on the material physical properties required for the composite biomaterial and a modulating organism, such as a bacteria, fungus or yeast, based on a desired effect of the modulating organism on the binding organism. As described in U.S. Pat. No. 10,125,347 a method is provided for stimulating the expression of specific tissue morphologies in filamentous fungi via interactions with competing microorganisms.

It is an object of the invention to incorporate reprogrammed (genetically engineered) bacterial and fungal components in a process of producing myceliated material.

It is another object of the invention to cohabitate both bacterial and fungal species together in a substrate of discrete particles and a nutrient material to improve existing processes of producing myceliated material and produce a new class of composite materials.

Briefly, the invention provides a process of making a biocomposite material utilizing a bacterial species and a fungal species in an agricultural feedstock composed of a substrate of non-nutrient discrete particles and a nutrient material wherein the bacterial species imparts mechanical properties to the biocomposite material and the fungal species binds the biocomposite material.

In accordance with the invention, both bacterium and fungus can be genetically engineered to produce desired properties within the microbial communities. This provides the ability to tightly regulate excreted compounds and fungal morphologies related to the production of antimicrobials, and final mechanical properties. This has also results in unique materials with a myriad of applications.

Bacterium Processing

In one embodiment, the process comprises the steps of forming a substrate of non-nutrient discrete particles and a nutrient material (i.e. a feedstock); adding a filamentous fungus to the substrate; adding a *Bacillus subtilis* strain characterized in producing a bio-film with poly-gamma-glutamic acid (PGA) to the substrate; and co-cultivating the fungus and the *Bacillus subtilis* strain in the substrate and allowing the fungus to digest the nutrient material in the substrate over a period of time sufficient to grow hyphae and to allow the hyphae to form a network of interconnected mycelia cells through and around all the non-nutrient discrete particles thereby bonding all the discrete particles together to form a self-supporting composite material.

This embodiment of the process produces a self-supporting biocomposite material comprising a substrate of non-nutrient discrete particles; a bio-film containing poly-gamma-glutamic acid (PGA) dispersed within the substrate; and a network of interconnected mycelia cells extending through and around the discrete particles and bonding the discrete particles together.

The bio-film containing poly-gamma-glutamic acid (PGA) dispersed within the substrate enhances the mechanical properties of the biocomposite material. For example, when feedstocks were co-cultivated with both fungus and PGA producing *Bacillus*, there was a demonstrated two-fold increase in the elastic modulus of the final material when compared to materials cultivated with only fungus.

In another embodiment, the process comprises the steps of forming a substrate of non-nutrient discrete particles and a nutrient material; adding a filamentous fungus to the substrate; adding a *Bacillus subtilis* strain characterized in producing melanin to the substrate; and co-cultivating the fungus and the *Bacillus subtilis* strain in the substrate and allowing the fungus to digest the nutrient material in the substrate over a period of time sufficient to grow hyphae and to allow the hyphae to form a network of interconnected mycelia cells through and around the non-nutrient discrete particles thereby bonding the discrete particles together to form a self-supporting composite material.

This embodiment of the process produces a self-supporting biocomposite material comprising a substrate of non-nutrient discrete particles; an amount of melanin dispersed within the substrate; and a network of interconnected mycelia cells extending through and around the discrete particles and bonding the discrete particles together.

The melanin dispersed within biocomposite material renders the biocomposite material radiation hard. Melanin is a complex molecule that is difficult to synthesize in vitro, and possesses energy absorption properties. By co-culturing a melanin producing bacteria within the composite material, one is able to manufacture melanin in situ. Once the composite is imbedded with melanin, the composite material is capable of absorbing UV and other types of radiation the material is exposed to, thus rendering the material radiation hard or resistant. The melanin imbedded material now has the capability to protect itself from dangerous radiation exposure, as well as protecting other living organisms i.e., humans, if the composite materials are used to build shelters or barriers were radiation is present i.e., laboratories or Mars.

In another embodiment, the process comprises the steps of forming a substrate of non-nutrient discrete particles and a nutrient material; adding a filamentous fungus to substrate; adding *Streptomyces natalensis* characterized in being able to produce natamycin during cultivation to the substrate; and co-cultivating the fungus and the *Streptomyces natalensis* in the substrate and allowing the fungus to digest the nutrient material in the substrate over a period of time sufficient to grow hyphae and to allow the hyphae to form a network of interconnected mycelia cells through and around the non-nutrient discrete particles thereby bonding the discrete particles together to form a self-supporting composite material while allowing the *Streptomyces natalensis* to produce natamycin in the self-supporting composite material.

This embodiment of the process produces a self-supporting biocomposite material comprising a substrate of non-nutrient discrete particles; an amount of natamycin dispersed within the substrate; and a network of interconnected mycelia cells extending through and around the discrete particles and bonding the discrete particles together.

The natamycin dispersed within biocomposite material imparts fungicidal properties to the biocomposite material and, in particular, renders a biocomposite material made with a filamentous fungus from the genus *Ganoderma* resistant to *Trichoderma*. Natamycin primarily targets fungi from the Ascomycota phylum. *Ganoderma* is from the Basidiomycota phylum.

In particular, the *Streptomyces* spp. is genetically engineered to produce a fungicidal agent that prevents *Trichoderma* spp. contamination when the material is bioactive i.e. during the manufacturing process, and throughout a living materials usable life span. This technique provides several advantages, namely, the technique
  a. enables non-sterile in-field cultivation practices through the reduction of contaminating microbes
  b. reduces bio-control infrastructure and sterile processes during manufacturing
  c. provides protection against contaminants such as *Trichoderma* during the usable life of "living materials".

In another embodiment, the process comprises the steps of forming a substrate of non-nutrient discrete particles and a nutrient material; adding a filamentous fungus to the substrate; adding a *Bacillus subtilis* strain characterized in producing Antifungal Protein (AFP1) native to *Streptomyces tendae* (previously characterized by Bormann, C., Baier, D., Horr, I., Raps, C., Berger, J., Jung, G., & Schwarz, H. (1999, Sep. 27, Characterization of a Novel, Antifungal, Chitin-Binding Protein from *Streptomyces tendae* Tu901 That Interferes with Growth Polarity. *Journal of Bacteriology*, 181 (24), 7421-7429) to the substrate; and co-cultivating the fungus and the *Bacillus subtilis* strain in the substrate and allowing the fungus to digest the nutrient material in the substrate over a period of time sufficient to grow hyphae and to allow the hyphae to form a network of interconnected mycelia cells through and around the non-nutrient discrete particles thereby bonding the discrete particles together to form a self-supporting composite material.

This embodiment of the process produces a self-supporting biocomposite material comprising a substrate of non-nutrient discrete particles; an amount of an antifungal protein (AFP1) native to *Streptomyces tendae* dispersed within the substrate; and a network of interconnected mycelia cells extending through and around the discrete particles and bonding the discrete particles together.

The antifungal protein (AFP1) dispersed within biocomposite material impacts fungicidal properties to the biocomposite material and, in particular, renders the biocomposite material resistant to *Trichoderma* as is the case with natamycin dispersed within the biocomposite material.

In each of the above described embodiments, the bacterial strain (i.e. microbial species) may be obtained from various sources. However, in accordance with the invention, the bacterial strain is obtained from the feedstock for making a biocomposite material. To this end, the invention provides a process of isolating a microbial species from a feedstock; genetically processing the microbial species and then returning the microbial species to the feedstock.

In accordance with the invention, this process comprises the steps of obtaining a feedstock including non-nutrient discrete particles, a nutrient material and at least one native microbial species; isolating the native microbial species from the feedstock; subjecting the isolated native microbial species to genetic processing to transform the native microbial species into a genetically engineered microbial species having predetermined characteristics; and thereafter returning the genetically engineered microbial species into the feedstock.

The native microbial species in the feedstock of interest would be one of *Bacillus* spp., *Streptomyces alboniger*, *Streptomyces natalensis*, and *Streptomyces tendae* and the characteristics of interest are one of producing a bio-film containing poly-gamma glutamic acid (PGA) in the feedstock, producing melanin in the feedstock, producing natamycin in the feedstock and producing an antifungal protein (AFP1) native to *Streptomyces tendae* in the feedstock.

Of note, *B. subtilis* has the ability to produce durable endospores which allows the *B. subtilis* to be used in co-inoculation. In this respect, the spore inoculum provides a robust precursor that can be prepared in advance to material cultivation, stored, transported, and more easily introduced into the feedstock during manufacturing particularly during infield deployment applications.

Fungal Processing

In accordance with the invention, the fungus for making a biocomposite material is genetically engineered to have predetermined characteristics.

In one embodiment, the filamentous fungus is genetically engineered to express carbonic anhydrase (CA) and the step of co-cultivating in the process of making a biocomposite material is performed in an environment without regulation of carbon dioxide ($CO_2$) through external inputs, such as, by using incubation chambers to regulate the carbon dioxide in the growth environment.

In another embodiment, the filamentous fungus is of the genus *Trametes* and is genetically engineered to overexpress chlamydospore production to increase the ability of the fungus to disperse through the growth substrate.

In another embodiment, the filamentous fungus is genetically engineered to overexpress a chitin deacetylase (DCA) gene to increase material strength in the formed self-supporting composite material. Overexpressing a chitin deacetylase gene in the fungal genome alters important structural components in the fungal cell wall i.e., chitin and chitosan. Modulating these ratios changes the mechanical properties of the cell wall and the final performance of the resultant biocomposite material when cultivated with these mutant strains.

In another embodiment, the filamentous fungus is of the genus *Ganoderma* and is genetically engineered to overexpress the production of hydrophobins to enhance the mycelium skin on the cells of the formed self-supporting composite material. Overexpressing hydrophobins (i.e. increasing the levels of hydrophobins) enhances the aesthetics of the resultant biocomposite material, produces a waterproofing skin encapsulating the material, which prevents water from entering the composite material, and resists swelling from humidity.

In another embodiment, the filamentous fungus is of the genus *Ganoderma* and is genetically engineered to overexpress the ortholog *Ganoderma* genes BGS1 and BGS2 that encode the two β-1,3-glucan synthases therein to increase glucans in the cells of the formed self-supporting composite material.

These and other objects of the invention will become more apparent from the following more detailed description.

DETAILED DESCRIPTION

The two current main production strains of filamentous fungus used in manufacturing processes to make a composite material according to U.S. Pat. No. 9,485,917, are members of the genus *Ganoderma* and *Trametes*, respectively.

Initially, two types of ATMT vectors were constructed, one type for use in *Ganoderma*, and another for use in *Trametes*. Each utilized the pOSCAR plasmid backbone developed for gene deletion in fungi. See Paz, Z., Garcia-Pedrajas, M. D., Andrews, D. L., Klosterman, S. J., Baeza-Montañez, L., Gold, S. E. (2011), One Step Construction of *Agrobacterium*-Recombination-ready-plasmids (OSCAR), an efficient and robust tool for ATMT based gene deletion construction in fungi. *Fungal Genet. Biol.* 48(7): 677-84.

Each vector had a hygromycin-resistance cassette regulated by the glyceraldehyde-3-phosphate dehydrogenase (GPD) controlling sequences native to that particular fungus. GPD has been used extensively to drive the expression of selectable markers in filamentous fungi, and in particular mushrooms (Kim et al., 2015, Current technologies and related issues for mushroom transformation. *Mycobiology*, 43(1): 1-8).

Use was made of two *Agrobacterium*-based transformation protocols for filamentous fungi found in the literature. One procedure was adapted from a protocol described by Kemppainen and Pardo (2011, Transformation of the mycorrhizal fungus *Laccaria bicolor* by using *Agrobacterium tumefaciens. Bioengineered Bugs* 2:1, 38-44) for the mushroom *Laccaria bicolor* and another used by Michielse et al. (2008 *Agrobacterium*-mediated transformation of the filamentous fungus *Aspergillus awamori. Nature Protocols* 3(10): 1671-1678) for the ascomycete fungus *Aspergillus awamori*.

Both fungal mycelia and fungal protoplasts (cell wall-less derivatives of mycelia) were used as the target tissue in the initial transformation experiments. Binary vector (pOSCAR) recombinant DNA plasmids were cloned in *E. coli*, and then transformed into *Agrobacterium tumefaciens* strain AGL-1, which already contained the Ti plasmid. The phenolic compound acetosyringone (AS) was used during the pre-cultivation of *A. tumefaciens* and also during co-cultivation with the fungus. Three different ratios of bacterium to fungus were used during co-cultivation, as well as three different temperatures (20° C., 22.5° C., 25° C.). After 4 days of co-cultivation, mycelia were transferred to selection plates, containing hygromycin at 50 μM to select for fungal transformants, and cefotaxin at 200 μM to select against *Agrobacterium*.

Work Flow of *Agrobacterium Tumefaciens* Mediated Transformation (ATMT)

Membranes were seeded with fungal mycelium, then infected with *A. tumefaciens* (AGL-1) harboring the recombinant DNA plasmid. Membranes with co-cultured Mycelium/AGL-1 were then transferred onto drug selection agar to remove AGL-1 and select for putative transformants. The mycelium was then sub-cultured for further isolation and PCR screening.

Transformation efficiencies between 15-30% were achieved using the ATMT platform with fungal mycelium.

Bacterium Processing

Identification and assembling of plasmids, controlling sequences, and drug marker cassettes for four primary bacterium strains were conducted Transformation protocols were also developed and optimized to allow for the efficient DNA transfer of these constructs (DNA sequences on the engineered plasmids) into each of our bacterium strains.

Engineering toolkits were developed for wild type isolates of *Bacillus* spp., *Streptomyces alboniger*, *Streptomyces natalensis*, and *Streptomyces tendae*. The "toolkits" involved the procedures for 1) cultivation in the lab i.e., temperatures, culture conditions 2) refined DNA transformation methods and 3) Gene controlling sequences used to engineer DNA plasmids which are then transformed into the bacteria.

Optimized transformation protocols for *Bacillus* spp. were based on inducing DNA uptake by nutrient starvation to increase the competency of recipient cells. These approaches were then tuned to overcome the more recalcitrant nature of non-domesticated strains through increased cell numbers and optimized competent cell preparations and media components.

Strong constitutive promoters were also identified, and used to drive expression in the overexpression plasmids. These technical achievements were then successfully used to engineer the *Bacillus* strains to produce melanin, PGA, antifungals, and confer drug resistance when co-cultivated with the fungus in agricultural feedstocks.

All three *Streptomyces* strains were cultivated at various temperatures to establish optimal growth conditions, in addition to best incubation conditions related to DNA conjugation protocols.

Bacterium Strain Engineering and Co-Cultivation

Using the toolkits for the bacterium community, these strains were engineered for enhanced material features by co-cultivation in feedstocks with the fungus.

One of the goals was to develop a novel microbial community that incorporates other soil microbes such as *Streptomyces* spp., and *Bacillus* spp. in farm waste inoculum. This more diversified community allowed the introduction of more complex, and novel properties into the resultant materials than were achieved using fungal species alone.

Co-Inoculating PGA Producing *Bacillus* Strains

Poly-gamma-glutamic acid (PGA) is a polypeptide, which consists of D- and L-glutamic acid units linked between amino and carboxyl groups.

Due to PGA's viscous, water soluble, and biodegradable properties, PGA has gained momentum in the fields of food science, agriculture, and biomedical devices. PGA is the primary constituent in the biofilm produced by some *Bacillus subtilis* strains.

The biofilm-producing *B. subtilis* strains were cohabited within our assembled microbiome.

Co-cultivating PGA producing *Bacillus* strains with the production fungus, leveraged the sticky viscus biofilm produced by the *Bacillus* to enhance the grown-in place bio-resin to significantly increase the flexure strength of the co-cultivated material by two-fold.

Co-Inoculating Melanin Producing *Bacillus* Strains

A melanin producing *Bacillus* strain was co-cultured with the fungus to produce a radiation hard material.

In this regard, a melanin expression pathway was engineered, then transformed into a *Bacillus* strain (ECO-ISO) isolated from a production feedstock.

The engineered *Bacillus* strain was co-cultivated with pre-myceliated feedstocks to produce a novel material with light and energy absorption properties. *Bacillus* was isolated from feedstocks, engineered to produce melanin, then introduced back into the community, and co-cultivated to add enhanced material properties.

*Streptomyces* spp., as a Co-Cultivation Chassis

In this particular case, the production fungus was co-inoculated with a strain of *Streptomyces natalensis* that provides substrates with fungicidal properties.

The goal in this case was to develop a cultivation paradigm that can utilize raw non-sterilized feedstocks. These biological controls could, in turn, reduce or eliminate the need for sterilization of raw agricultural substrates prior to inoculation and provide relief for sterile controls throughout the material growth cycle and manufacturing process.

Eliminating the need for sterilization provides significant energy savings during manufacture. Also, these biomaterials could be grown and produced outside of a manufacturing facility, thus reducing infrastructure, and enabling "in field" production using various low-quality agriculture substrates specific to the region.

*Streptomyces natalensis* naturally produces low levels of pimaricin, also known as natamycin, which is a fungicide with the ability to bind to sterols found in fungal cell membranes, thus making the cell wall permeable and lysing the cell. This fungicide has greater activity against Ascomycete contaminants, versus production fungi *Ganoderma* or *Trametes*. Natamycin's affinity for non-basidiomycetes species make this particular antifungal an attractive target for expression during cultivated manufacturing.

The overexpression of the pimM protein was engineered. This pimM protein has been characterized as a positive regulator for the natamycin biosynthesis gene cluster. See Anton, A., Santos-Aberturas, J., Mendes, M. V., Guerra, S. M., Martin, J. F., Aparicio, J. F. (2007). PimM, a PAS domain positive regulator of pimaricin biosynthesis in *Streptomyces natalensis*. Microbiology 153, 3174-3183.

By up-regulating the expression of pimM, the total yield of natamycin produced by our *Streptomyces natalensis* strains was increased. In this respect, natamycin production in wild type *Streptomyces natalensis* is within the effective range of inhibition (5 ug/mL) when cultured in vitro (liquid media). However, the production of natamycin must be increased to produce a more potent drug titer in co-cultivated feedstocks. Engineering a bacterium strain with increased natamycin potency helps to reduce the bacterial loading needed for substrate bioburden mitigation, thus further reducing process and material cost.

A pimM overexpression construct was designed and cloned using *Streptomyces* specific constitutive promoter (ermE) and a second expression construct was designed and cloned utilizing the native pimM promoter sequence.

The constructs were constructed using Gibson Assembly and subcloned into DH5a, and then transformed into a DNA donor non-methylation *E. coli* strain. A conjugation protocol was optimized to transform the DNA constructs into the unique *Streptomyces* strain.

Due to the complexities and diversification of *Streptomyces* species, there is no universal standard protocol that works efficiently with all *Streptomyces* spp. Accordingly, a spore harvesting technique (determined spores are best DNA recipients) was developed and optimized and a conjugation method was developed and optimized for non-domesticated *Streptomyces* strains.

The conjugation protocol was implemented to transform the pimM constructs from the *E. coli* donor strain into *S. natalensis*.

The efficacy of inhibitory properties was tested in feedstocks without the addition of the fungus. Feedstocks were loaded with *Trichoderma* spores, a common mold contaminate. Engineered *Streptomyces* was then co-cultured in these contaminated feedstocks, and the inhibitory effects were recorded. A strong linear inhibitory effect of *Trichoderma* in feedstocks was demonstrated as a function of natamycin expression.

A *Bacillus* strain was engineered to express an antifungal protein (AFP1) native to *Streptomyces tendae*. AFP1 is a more attractive protein for expression in a non-native host than natamycin based on its simple expression pathway. AFP1 is produced by the expression of a single protein (87 amino acids). This antifungal protein is of particular interest because of its resistance to degradation in harsh environments. AFP1 is stable over a pH range of 1.5-12, is highly resistant to digestion via peptidases, and can retain 50% of the antifungal activity after 60 min heat treatments of 70-100° C.

*Bacillus* AFP1 overexpression plasmids were designed by cloning our *Streptomyces* AFP1-Mature sequence into our *Bacillus* backbone p1664. The mature version of the AFP1 sequence has been truncated (42 AA cleavage) to eliminate the need for post-translational modifications. A strong constitutive promoter Pveg with an optimized ribosomal binding site was cloned in front of the AFP1 ORF to drive expression. The full expression sequence was cloned between a 5' and 3' flanking region for the thrC locus native to *Bacillus* spp. Taking advantage of homologous recombination, we integrated our expression sequence into the thrC gene of the *Bacillus* genome.

Once the plasmid was assembled using Gibson Assembly, the plasmid was transformed into 10-Beta *E. coli* cells for propagation. The plasmid was then isolated and verified by PCR, digestion, and sanger sequencing. The sequence verified plasmid was then transformed into two different *Bacillus* strains; *Bacillus subtilis*_168 (B.s_168), and *Bacillus subtilis*_KO7 (B.s_KO7). B.s_168 is a common lab strain that we have already been able to co-cultivate with our fungus in feedstocks.

Putative transformants were recovered by drug selection plating, and PCR verified.

To determine if our constructs were successfully expressing AFP1 in *Bacillus*, we performed Sq-RT-PCR to test the AFP1 transcription levels in our engineered strains. Both engineered strains had robust AFP1 transcription levels, and the non-engineered wild type strains had no detectable expression as expected.

To establish the effectiveness of *Bacillus* KO7_AFP1 as an antifungal agent when co-cultivated in our agricultural feedstocks, we performed experiments where we co-cultured both our *Bacillus* KO7_AFP1 strain ($1\times10^8$ bac/1 g dry feedstock) and *Trichoderma* spores in standard feedstock blends of Ecovative Design, LLC of Green Island, N.Y., without the addition of a production fungus. The exclusion of fungus was intentionally done to eliminate any possible community interactions between the native fungal defense mechanisms (i.e., the secretion of antimicrobial compounds) which could interfere with the interpretation of the *Bacillus* KO7_AFP1 inhibitory effects.

Three experimental sets were prepared for each experiment; 1) *Trichoderma* spores only, 2) *Trichoderma* spores co-cultured with the empty vector *Bacillus* strain KO7, and 3) *Trichoderma* spores co-cultured with *Bacillus* KO7_AFP1.

The *Trichoderma* spore load remained constant across sets, and was orders of magnitude higher than typical ambient contamination titers. Once feedstocks were inoculated, the material was allowed to incubate at standard incubation parameters of Ecovative Design, LLC.

Samples were visually inspected for *Trichoderma* sporulation over the course of ten days. We observed complete *Trichoderma* inhibition in the feedstocks through the first six days when co-cultured with *Bacillus* KO7_AFP1, after which point, *Trichoderma* began to sporulate throughout the co-cultured feedstocks at reduced rates when compared to the *Trichoderma* only control sets. This six day window of mold inhibition provides ample time to allow a co-cultivated fungus to fully colonize the feedstocks and out compete any bioburden molds that may reside within the feedstocks at inoculation.

In addition to determining the inhibitory properties of *Bacillus* KO7_AFP1 as it relates to bioburden (*Trichoderma* spp.), we needed to assess the potential for any significant inhibition of the production fungus when co-cultured in feedstocks with *Bacillus KO*7_AFP1.

Standard Ecovative feedstock materials (blends) were co-inoculated with production fungus (*Ganoderma* spp.) and cultured *Bacillus* KO7 AFP1 at $1\times10^8$ bac/1 g dry feedstock. The material was cultivated using Ecovative's manufacturing guidelines, and grown into 2"×6"×6" testing plaques. The co-cultivated material was then tested for mechanical properties; ASTM D1621-16. Material co-cultured with *Bacillus* KO7 (chassis control) and *Bacillus* KO7_APF1 (AFP1 expression) yielded no significant detrimental effects on compressive modulus (composite strength). The high inoculation titers of chassis bacteria did not reduce fungal colonization even in the presence AFP1 expression.

We successfully demonstrated the construction of a *Bacillus* KO7_AFP1 strain capable of expressing high titers of AFP1 protein. We further demonstrated the ability of our engineered strain to inhibit known bioburden molds (i.e., *Trichoderma* spp., and *C. sitophila*) isolated in the facilities and manufacturing process of Ecovative Design using plate based assays, and competition assays in our production feedstock blends.

*Bacillus* KO7 has been successfully co-cultured with the Ecovative production fungus on feedstocks without any negative effects on fungal colonization and final material mechanical properties while maintaining high viable bacterium survivability in the microbial community. Additionally, when AFP1 is expressed in situ by this new *Bacillus* chassis, we observed no detrimental effects on fungal growth and material performance.

Fungal Strain Engineering

A fungal network was engineered to bind the feedstock matrix.

Leveraging the co-cultivation platforms and fungal strain engineering provides for increased growth and enhanced proliferation of a mycelium network throughout the inoculated feedstocks, and increased resistance to competing microbes native to the feedstocks or contaminants encountered during scaled cultivation.

Several fungal strains were genetically engineered to increase performance in the bio-manufacturing process as described in U.S. Pat. No. 9,485,917 through the increased distribution of inoculum spores in feedstocks and the upregulation of carbonic anhydrase (CA) to help reduce environmental cultivation infrastructure.

The upregulation of cell surface hydrophobins, B-glucans, and chitosan was performed to increase fungal resin properties and enhance material performance i.e., strength, and water resistance.

Enhanced Manufacturing Process—nrg1 and efg1 Regulation (Chlamydospore)

Chlamydospores are produced by some fungi as a survival strategy when exposed to harsh environmental conditions (nutrient depletion, temperature variations). From a practical point of view, these spores enable production of an inoculum using *Trametes* sp. that is more resistant to contamination, with the increased ability to disperse throughout the substrate providing better acquisition of available resources.

The spore induction pathway was engineered by overexpressing a positive transcriptional regulator egf1, and knocking out a negative transcriptional regulator gene sequence nrg1. Both efg1 overexpression, and nrg1 knockout strains were made.

Using an alternative approach to upregulating chlamydospore production in *Trametes* by overexpression of a positive regulator, a plasmid was designed and cloned with the potential to knockout the ortholog of nrg1, characterized as a negative transcriptional regulator in the chlamydospore induction pathway.

The knockout strategy was designed around homologous recombination. A hygromycin drug cassette was cloned between a 5' and 3' flanking region of the nrg1 gene. This setup allowed recombination between the homologous flanking regions thus flipping the drug cassette into the nrg1 ORF effectively interrupting or knocking out the gene.

Microscopy was performed to characterize the nrg1_KO mutant. The nrg1_KO was grown on ME agar for three days, then sampled for characterization on bright field microscopy to evaluate asexual spore formation. Knocking out nrg1 significantly upregulated the production of asexual anthrospores. Anthrospores are asexual spores that form in monokaryon basidiomycete fungus. When compared, the relative numbers of anthrospores between the wild type and nrg1_KO showed a 42% increase in asexual spore formation in the mutant.

The growth rate of nrg1_KO was also measured and compared to the wild type. Both the nrg1_KO and wild type were inoculated onto the center of ME agar plates in triplicate, and incubated at 24° C. The total area of growth was measured over a period of five days. A significant increase was observed in the growth rate of the nrg1_KO when compared to the wild type. Here, a more robust, faster growing strain was observed from the deletion of nrg1.

The macro-morphology of the nrg1_KO is also distinctly different from the wild type. The wild type maintains uniform and tight leading-edge growth, while the mutant displays a more reaching non-uniform morphology. This phenotype is typically associated with a nutritional "searching" behavior.

Enhanced Material Performance-Chitin Deacetylase (CDA) Expression

Fungi cell walls consist in part of glycoproteins, hydrophobins, chitin, and chitosan. The ratio of all these constituents contributes to cell wall structure (i.e., mechanical properties, and permeability). Chitosan is derived through the deacetylation of nascent chitin by various chitin deacetylase (CDA) proteins which hydrolyze the acetamido group in the N-acetylglucosamine units of chitin, thus generating glucosamine units and acetic acid.

A chitin deacetylase overexpression plasmid was engineered and cloned.

The plasmid contained the CDA1 ORF cloned from *Saccharomyces cerevisiae* S288c, and the expression driven by the glyceraldehyde-3-phosphate dehydrogenase GPD promoter.

The *S. cerevisiae* CDA1 gene was the first chitin deacetylase gene identified, and its function has been characterized using both in vitro and in vivo models. Assembled constructs were transformed into a production fungus and verified by PCR.

For each of the two mutants used, the insertion of the CDA1 expression construct was positioned at different sites within the fungal genome. In fungal genomes, it is not uncommon for expression levels of the same genes to be different when expressed from different locations on the genome. Because of this, both transformants generated from the same plasmid were screened. Each strain was characterized for micro-morphology, growth rates, antifungal properties, and the mechanical strength of material generated by these strains.

Feedstocks were inoculated with each strain, and cultivated in bags and then in plastic molds (tools) to set the geometry for mechanical testing plaques. On visual observation, all strains colonized the feedstocks well and in similar fashion.

Materials cultivated from the engineered CDA strains were tested for their mechanical properties (compressive modulus) and compared to a wild type strain. Compressive modulus is a function of material stiffness and a standard metric used to assess material strength.

Material cultivated with the CDA1.18-3 strain, had significantly higher compressive modulus when compared to both wild type and CDA1.14-2. No significant differences were observed between CDA1.14-2 and the wild type.

Material cultivated with the CDA1.18-4 engineered strain was significantly stronger (compressive modulus) than material grown with the wild type strain.

Enhanced Material Performance—frt1 Regulation (Hydrophobins)

Hydrophobins are cysteine rich proteins that are anchored on the outer surface of fungal cell walls. These proteins give the outside surface of the cell its hydrophobic properties. Hydrophobins are unique to fungi, and are linked to growth morphology and cell signaling.

Two separate publicly available materials from Ecovative Design, LLC of Green Island, N.Y., were cultivated using unique cultivation paradigms and agricultural feedstock blends; 1) Ecovative's standard MycoComposite™ mycelium bound agricultural byproduct sold as "Protective Packaging" used as protective packaging or molded shapes, 2) Ecovative's MycoComposite™ 584 structural material used for construction building material.

Each of the two materials were cultivated and processed to either induce or reduce the amount of the mycelium skin that encapsulates the final forms. By reducing or inducing the amount of mycelium skin, we can quantitate the effects of the hydrophobin layer as a function of water absorption.

For standard MycoComposite™ Protective Packaging materials, environmental conditions such as temperature, $CO_2$, and relative humidity (RH) were tuned to drive mycelial growth to the outer surface of the material. As such, Ecovative's structural materials were grown in conditions which enabled optimal internal colonization to add overall mechanical strength properties, thus reducing the external myceliation and reducing the hydrophobin skin on the surface of the material.

Once testing plaques were grown and processed to either reduce or induce the quantity of mycelium skin on the surface of the parts, they were subjected to water submersion testing (ASTM C1134). Parts were measured (physical dimensions and weight) and then submerged into a water tank. The plaques were held to complete submersion for 24 hours, then removed and re-measured. The percent of water mass absorbed was calculated and plotted for each of the two materials with variable mycelium skins. Water absorption of the standard Structural material was measured at 35% water mass absorption, but when the hydrophobic skin was reduced, there was a 61% water mass absorption for the material. This is a 43% increase in water absorption.

Standard MycoComposite™ Protective Packaging material was measured at a 15% water mass absorption, but significantly increased to 55% when the hydrophobic skin was removed demonstrating a staggering 77% increase in water absorption.

The amount of hydrophobic mycelium skin coating the part is proportional to the percent of water absorption. Both materials have similar absorption performance at reduced skin formats, but the MycoComposite™ Protective Packaging material performs better than the structural material in the induced hydrophobin skin sets. One explanation for this difference would be the paradigm which MycoComposite™ Protective Packaging is grown when compared to the Structural materials. MycoComposite™ Protective Packaging is cultivated to "force" myceliation to the outer surfaces of the material to aid in aesthetics (softer feel), and to promote "cushioning" properties gained with reduced internal colonization.

As for MycoComposite™ 584 structural materials, they are primarily cultivated to increase internal colonization with limited surface flush, thus enhancing mechanical properties such as internal bond and modulus. Engineering the fungus to increase hydrophobin production while still driving internal part colonization enables the growth of strong structural materials while retaining some of the critical mycelium hydrophobins on the surface of the material to protect the grown material from the elements.

Enhanced Material Performance—Regulation of β-Glucans

Glucans are the major structural polysaccharides of the fungal cell wall, constituting approximately 50-60% of the wall by dry weight. These polysaccharides are of particular interest with regards to increasing the internal bond strength of composites through enhanced fungal resin properties. The most abundant glucan in the fungal cell wall is β-1,3-glucan, which makes up between 65% and 90% of the whole β-glucan content.

Recombinant DNA constructs were made with the goal of over-expressing the genes (BGS1 and BGS2) that encode the two β-1,3-glucan synthases found in the *Ganoderma* genome. Use was made of the controlling sequences from the constitutively-expressed gene encoding glyceraldehyde-3-phosphate dehydrogenase (GPD) to drive expression of BGS1 and BGS2.

These constructs were used in classical PEG-mediated co-transformation experiments using a second plasmid containing a resistance gene to the fungicide carboxin. Three carboxin-resistant co-transformants were verified via PCR to have the integrated BGS overexpression constructs: two with BGS1 (BGS1-1, 1-7), and a third with BGS2 (BGS2-1). Assays for glucan content suggested a significant increase in the β-glucan fraction in each of the three co-transformants (i.e. 165%, 135%, and 147%, respectively).

The engineered *Ganoderma*_BGS strains had about a two-fold increase in β-1,3-glucan levels in the cell wall fractions when compared to the unmodified wild type *Ganoderma*.

The invention thus provides unique techniques for incorporating reprogrammed (genetically engineered) bacterial and fungal components in a process of producing myceliated material.

The invention also provides a process of cohabitating both bacterial and fungal species together in a substrate of discrete particles and a nutrient material to improve existing processes of producing myceliated material and produce a new class of composite materials.

What is claimed is:

1. A process comprising:
   obtaining a feedstock including non-nutrient discrete particles, a nutrient material and at least one native microbial species;
   isolating said at least one native microbial species from said feedstock;
   subjecting said isolated native microbial species to genetic processing to transform said native microbial species into a genetically engineered microbial species having predetermined characteristics;
   thereafter returning said genetically engineered microbial species into said feedstock; and
   cohabitating at least one filamentous fungal species with said genetically engineered microbial species in the feedstock, thereby producing a biocomposite material with desired properties.

2. The process of claim 1, wherein said native microbial species is at least one of *Bacillus* spp. and *Streptomyces* spp.

3. The process of claim 2, wherein at least one of said characteristics is producing a bio-film containing poly-gamma-glutamic acid in said feedstock, producing natamycin in said feedstock and producing an antifungal protein (AFP1) native to *Streptomyces tendae* in said feedstock.

4. The process of claim 2, wherein said native microbial species is *Bacillus* spp.

5. The process of claim 4, wherein at least one of said characteristics is producing a bio-film containing poly-gamma-glutamic acid in said feedstock.

6. The process of claim 4, wherein at least one of said characteristics is producing natamycin in said feedstock.

7. The process of claim 4, wherein at least one of said characteristics is producing an antifungal protein (AFP1) native to *Streptomyces tendae* in said feedstock.

8. The process of claim 2, wherein said native microbial species is *Streptomyces* spp.

9. The process of claim 8, wherein said native microbial species is *Streptomyces natalensis*.

10. The process of claim 9, wherein at least one of said characteristics is producing a bio-film containing poly-gamma-glutamic acid in said feedstock.

11. The process of claim 9, wherein at least one of said characteristics is producing natamycin in said feedstock.

12. The process of claim 9, wherein at least one of said characteristics is producing an antifungal protein (AFP1) native to *Streptomyces tendae* in said feedstock.

13. The process of claim 8, wherein said native microbial species is *Streptomyces tendae*.

14. The process of claim 13, wherein at least one of said characteristics is producing a bio-film containing poly-gamma-glutamic acid in said feedstock.

15. The process of claim 13, wherein at least one of said characteristics is producing natamycin in said feedstock.

16. The process of claim 13, wherein at least one of said characteristics is producing an antifungal protein (AFP1) native to *Streptomyces tendae* in said feedstock.

17. The process of claim 8, wherein said native microbial species is *Streptomyces alboniger*.

18. The process of claim 17, wherein at least one of said characteristics is producing a bio-film containing poly-gamma-glutamic acid in said feedstock.

19. The process of claim 17, wherein at least one of said characteristics is producing natamycin in said feedstock.

20. The process of claim 17, wherein at least one of said characteristics is producing an antifungal protein (AFP1) native to *Streptomyces tendae* in said feedstock.

21. The process of claim 1, wherein obtaining comprises obtaining the feedstock further including the at least one filamentous fungal species.

22. The process of claim 1, further comprising subjecting said filamentous fungal species to genetic processing to transform said filamentous fungal species into a genetically engineered filamentous fungal species having predetermined characteristics.

23. The process of claim 22, wherein returning further comprises returning said genetically engineered filamentous fungal species into said feedstock.

24. The process of claim 1, wherein said desired properties is at least one of mechanical properties, morphological properties, and antimicrobial properties.

* * * * *